(12) United States Patent
Blau et al.

(10) Patent No.: US 8,586,294 B2
(45) Date of Patent: Nov. 19, 2013

(54) DETECTION OF PROTEIN TRANSLOCATION BY BETA-GALACTOSIDASE REPORTER FRAGMENT COMPLEMENTATION

(75) Inventors: Helen M. Blau, Menlo Park, CA (US); Thomas S. Wehrman, Redwood City, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 150 days.

(21) Appl. No.: 11/132,764

(22) Filed: May 18, 2005

(65) Prior Publication Data

US 2005/0287522 A1 Dec. 29, 2005

Related U.S. Application Data

(60) Provisional application No. 60/572,635, filed on May 18, 2004.

(51) Int. Cl.
| | |
|---|---|
| *C12Q 1/68* | (2006.01) |
| *C12Q 1/70* | (2006.01) |
| *G01N 33/53* | (2006.01) |
| *G01N 33/536* | (2006.01) |

(52) U.S. Cl.
USPC ............... 435/5; 435/455; 435/456; 435/7.92

(58) Field of Classification Search
None
See application file for complete search history.

(56) References Cited

U.S. PATENT DOCUMENTS

| | | | | |
|---|---|---|---|---|
| 5,362,625 | A  * | 11/1994 | Krevolin et al. ............... | 435/7.6 |
| 6,428,951 | B1 * | 8/2002 | Michnick et al. ................ | 435/4 |
| 6,432,403 | B1 * | 8/2002 | Philips ....................... | 424/134.1 |
| 6,727,070 | B2 * | 4/2004 | Thomas et al. ................ | 435/7.1 |
| 2001/0047526 | A1 * | 11/2001 | Brisson et al. ............... | 800/298 |

FOREIGN PATENT DOCUMENTS

| | | |
|---|---|---|
| EP | 1076097 A1 | 2/2001 |
| EP | 1132092 A1 | 9/2001 |
| WO | 8602666 A1 | 5/1986 |
| WO | 02/29410 | 4/2002 |
| WO | 02/099381 | 12/2002 |

OTHER PUBLICATIONS

Potrykus, Gene transfer to cereals: an assessment, Biotechnology, 1990, 8(6):535-542.*
Ngo et al., in The Protein Folding Problem and Tertiary Structure Prediction, 1994, Merz et al. (ed.), Birkhauser, Boston, MA, pp. 433 and 492-495.*
Bonifaci et al. AIDS. Sep. 1995;9(9):995-1000.*
Floyd, D., et al., "C5a receptor oligomerization," (2003) The Journal of Biological Chemistry, 278(37):35354-35361.
Graham, D., et al., "Application of B-galactosidase enzyme complementation technology as a high throughput screening format for antagonists of the epidermal growth factor receptor," (2001) Journal of Molecular Screening, 6 (6):401-411.
Ngo, J., et al., "Computational complexity, protein structure prediction, and the Levinthal paradox," (1994) The Protein Folding Problem and Tertiary Structure Prediction, Mers & Le Grand, eds., 491-495.
Eglen, Richard M., "Enzyme Fragment Complementation: A Flexible High Throughput Screening Assay Technology", Assay and Drug Development Technologies, 2002, 1(1):97-104.
Wehrman, Tom S., et al., "Enzymatic detection of protein translocation," Nature Methods, vol. 2, No. 7, pp. 521-527 (Jun. 22, 2005).
European Search Report, Application No. 05751854.0 dated Feb. 3, 2012.
Eglen, Richard M., "Beta Galactosidase Enzyme Fragment Complementation as A Novel Technology for High Throughput Screening," Combinatorial Chemistry & High Throughput Screening, 2003, vol. 6, pp. 381-387.

* cited by examiner

*Primary Examiner* — Lisa J Hobbs
(74) *Attorney, Agent, or Firm* — David J. Aston; Peters Verny, LLP

(57) ABSTRACT

Methods and compositions are provided for detecting molecular translocations, particularly protein translocations within and between subcellular copartments, using at least two components that exhibit a localization-dependent difference in complementation activity. In particular, alpha-complementing β-galactosidase fragments are provided. These β-galactosidase reporter fragments display significantly enhanced enzymatic activity when one fragment is localized in a membrane. Methods for carrying out no-wash ELISA assays based on the reporter component system are also provided.

19 Claims, 7 Drawing Sheets

Fig.5
A) 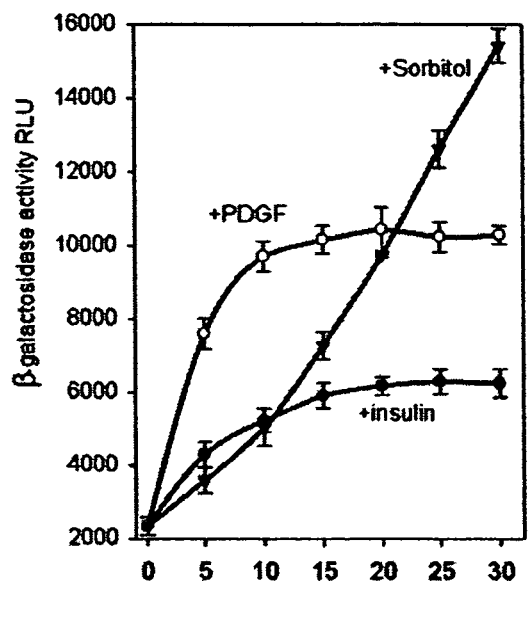
B) 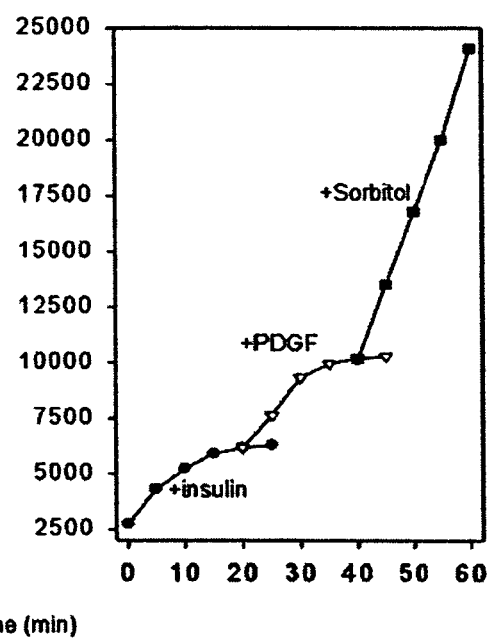
Time (min)

```
                        SEQUENCE LISTING

<160> NUMBER OF SEQ ID NOS: 12

<210> SEQ ID NO 1
<211> LENGTH: 52
<212> TYPE: PRT
<213> ORGANISM: Escherichia coli
<220> FEATURE:
<223> OTHER INFORMATION: alpha peptide (wildtype)

<400> SEQUENCE: 1

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 2
<211> LENGTH: 52
<212> TYPE: PRT
<213> ORGANISM: Escherichia coli
<220> FEATURE:
<223> OTHER INFORMATION: alpha peptide (H31R)

<400> SEQUENCE: 2

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala Arg Pro
```

```
                20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 3
<211> LENGTH: 52
<212> TYPE: PRT
<213> ORGANISM: Escherichia coli
<220> FEATURE:
<223> OTHER INFORMATION: alpha peptide (F34Y)

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Tyr Ala Ser Trp Arg Asn Ser Glu Glu Ala Arg Thr Asp Arg Pro
        35                  40                  45

Ser Gln Gln Leu
    50

<210> SEQ ID NO 4
<211> LENGTH: 52
<212> TYPE: PRT
<213> ORGANISM: Escherichia coli
<220> FEATURE:
<223> OTHER INFORMATION: alpha peptide (E41Q)

<400> SEQUENCE: 4

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Gln Glu Ala Arg Thr Asp Arg Pro
        35                  40                  45

Ser Gln Gln Leu
    50

<210> SEQ ID NO 5
<211> LENGTH: 52
<212> TYPE: PRT
<213> ORGANISM: Escherichia coli
<220> FEATURE:
<223> OTHER INFORMATION: alpha-peptide (N39D)

<400> SEQUENCE: 5

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asp Ser Glu Glu Ala Arg Thr Asp Arg Pro
        35                  40                  45

Ser Gln Gln Leu
    50

<210> SEQ ID NO 6
<211> LENGTH: 43
<212> TYPE: PRT
<213> ORGANISM: Escherichia coli
<220> FEATURE:
```

-continued

<223> OTHER INFORMATION: alpha-peptide (truncated)

<400> SEQUENCE: 6

```
Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala
        35                  40
```

<210> SEQ ID NO 7
<211> LENGTH: 993
<212> TYPE: PRT
<213> ORGANISM: Escherichia coli
<220> FEATURE:
<223> OTHER INFORMATION: exemplary omega-peptide

<400> SEQUENCE: 7

```
Met Gly Val Ile Thr Asp Ser Leu Ala Val Val Ala Arg Thr Asp Arg
1               5                   10                  15

Pro Ser Gln Gln Leu Arg Ser Leu Asn Gly Glu Trp Arg Phe Ala Trp
            20                  25                  30

Phe Pro Ala Pro Glu Ala Val Pro Glu Ser Trp Leu Glu Cys Asp Leu
        35                  40                  45

Pro Glu Ala Asp Thr Val Val Pro Ser Asn Trp Gln Met His Gly
    50                  55                  60

Tyr Asp Ala Pro Ile Tyr Thr Asn Val Thr Tyr Pro Ile Thr Val Asn
65                  70                  75                  80

Pro Pro Phe Val Pro Thr Glu Asn Pro Thr Gly Cys Tyr Ser Leu Thr
                85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
        115                 120                 125

Val Gly Tyr Gly Gln Asp Ser Arg Leu Pro Ser Glu Phe Asp Leu Ser
    130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
        195                 200                 205

Val Leu Glu Ala Glu Val Gln Met Cys Gly Glu Leu Arg Asp Tyr Leu
    210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
            260                 265                 270

Ala Glu Ile Pro Asn Leu Tyr Arg Ala Val Val Glu Leu His Thr Ala
        275                 280                 285

Asp Gly Thr Leu Ile Glu Ala Glu Ala Cys Asp Val Gly Phe Arg Glu
    290                 295                 300
```

-continued

```
Val Arg Ile Glu Asn Gly Leu Leu Leu Asn Gly Lys Pro Leu Leu
305                 310                 315                 320

Ile Arg Gly Val Asn Arg His Glu His His Pro Leu His Gly Gln Val
            325                 330                 335

Met Asp Glu Gln Thr Met Val Gln Asp Ile Leu Leu Met Lys Gln Asn
            340                 345                 350

Asn Phe Asn Ala Val Arg Cys Ser His Tyr Pro Asn His Pro Leu Trp
            355                 360                 365

Tyr Thr Leu Cys Asp Arg Tyr Gly Leu Tyr Val Val Asp Glu Ala Asn
370                 375                 380

Ile Glu Thr His Gly Met Val Pro Met Asn Arg Leu Thr Asp Asp Pro
385                 390                 395                 400

Arg Trp Leu Pro Ala Met Ser Glu Arg Val Thr Arg Met Val Gln Arg
                405                 410                 415

Asp Arg Asn His Pro Ser Val Ile Ile Trp Ser Leu Gly Asn Glu Ser
            420                 425                 430

Gly His Gly Ala Asn His Asp Ala Leu Tyr Arg Trp Ile Lys Ser Val
            435                 440                 445

Asp Pro Ser Arg Pro Val Gln Tyr Glu Gly Gly Gly Ala Asp Thr Thr
450                 455                 460

Ala Thr Asp Ile Ile Cys Pro Met Tyr Ala Arg Val Asp Glu Asp Gln
465                 470                 475                 480

Pro Phe Pro Ala Val Pro Lys Trp Ser Ile Lys Lys Trp Leu Ser Leu
                485                 490                 495

Pro Gly Glu Thr Arg Pro Leu Ile Leu Cys Glu Tyr Ala His Ala Met
            500                 505                 510

Gly Asn Ser Leu Gly Gly Phe Ala Lys Tyr Trp Gln Ala Phe Arg Gln
            515                 520                 525

Tyr Pro Arg Leu Gln Gly Gly Phe Val Trp Asp Trp Val Asp Gln Ser
530                 535                 540

Leu Ile Lys Tyr Asp Glu Asn Gly Asn Pro Trp Ser Ala Tyr Gly Gly
545                 550                 555                 560

Asp Phe Gly Asp Thr Pro Asn Asp Arg Gln Phe Cys Met Asn Gly Leu
                565                 570                 575

Val Phe Ala Asp Arg Thr Pro His Pro Ala Leu Thr Glu Ala Lys His
            580                 585                 590

Gln Gln Gln Phe Phe Gln Phe Arg Leu Ser Gly Gln Thr Ile Glu Val
            595                 600                 605

Thr Ser Glu Tyr Leu Phe Arg His Ser Asp Asn Glu Leu Leu His Trp
610                 615                 620

Met Val Ala Leu Asp Gly Lys Pro Leu Ala Ser Gly Glu Val Pro Leu
625                 630                 635                 640

Asp Val Ala Pro Gln Gly Lys Gln Leu Ile Glu Leu Pro Glu Leu Pro
                645                 650                 655

Gln Pro Glu Ser Ala Gly Gln Leu Trp Leu Thr Val Arg Val Val Gln
            660                 665                 670

Pro Asn Ala Thr Ala Trp Ser Glu Ala Gly His Ile Ser Ala Trp Gln
            675                 680                 685

Gln Trp Arg Leu Ala Glu Asn Leu Ser Val Thr Leu Pro Ala Ala Ser
            690                 695                 700

His Ala Ile Pro His Leu Thr Thr Ser Glu Met Asp Phe Cys Ile Glu
705                 710                 715                 720

Leu Gly Asn Lys Arg Trp Gln Phe Asn Arg Gln Ser Gly Phe Leu Ser
                725                 730                 735
```

Gln Met Trp Ile Gly Asp Lys Lys Gln Leu Leu Thr Pro Leu Arg Asp
                740                 745                 750

Gln Phe Thr Arg Ala Pro Leu Asp Asn Asp Ile Gly Val Ser Glu Ala
            755                 760                 765

Thr Arg Ile Asp Pro Asn Ala Trp Val Glu Arg Trp Lys Ala Ala Gly
770                 775                 780

His Tyr Gln Ala Glu Ala Ala Leu Leu Gln Cys Thr Ala Asp Thr Leu
785                 790                 795                 800

Ala Asp Ala Val Leu Ile Thr Thr Ala His Ala Trp Gln His Gln Gly
                805                 810                 815

Lys Thr Leu Phe Ile Ser Arg Lys Thr Tyr Arg Ile Asp Gly Ser Gly
            820                 825                 830

Gln Met Ala Ile Thr Val Asp Val Glu Val Ala Ser Asp Thr Pro His
        835                 840                 845

Pro Ala Arg Ile Gly Leu Asn Cys Gln Leu Ala Gln Val Ala Glu Arg
850                 855                 860

Val Asn Trp Leu Gly Leu Gly Pro Gln Glu Asn Tyr Pro Asp Arg Leu
865                 870                 875                 880

Thr Ala Ala Cys Phe Asp Arg Trp Asp Leu Pro Leu Ser Asp Met Tyr
                885                 890                 895

Thr Pro Tyr Val Phe Pro Ser Glu Asn Gly Leu Arg Cys Gly Thr Arg
            900                 905                 910

Glu Leu Asn Tyr Gly Pro His Gln Trp Arg Gly Asp Phe Gln Phe Asn
        915                 920                 925

Ile Ser Arg Tyr Ser Gln Gln Gln Leu Met Glu Thr Ser His Arg His
930                 935                 940

Leu Leu His Ala Glu Glu Gly Thr Trp Leu Asn Ile Asp Gly Phe His
945                 950                 955                 960

Met Gly Ile Gly Gly Asp Asp Ser Trp Ser Pro Ser Val Ser Ala Glu
                965                 970                 975

Phe Gln Leu Ser Ala Gly Arg Tyr His Tyr Gln Leu Val Trp Cys Gln
            980                 985                 990
Lys

<210> SEQ ID NO 8
<211> LENGTH: 52
<212> TYPE: PRT
<213> ORGANISM: Escherichia coli
<220> FEATURE:
<223> OTHER INFORMATION: exemplary high affinity peptide

<400> SEQUENCE: 8

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu
    50

<210> SEQ ID NO 9
<211> LENGTH: 52
<212> TYPE: PRT
<213> ORGANISM: Escherichia coli
<220> FEATURE:
<223> OTHER INFORMATION: exemplary high affinity peptide

<400> SEQUENCE: 9

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Tyr Arg Asn Ser Glu Glu Ala Arg Thr Asp Arg Pro
        35                  40                  45

Ser Gln Gln Leu
    50

<210> SEQ ID NO 10
<211> LENGTH: 53
<212> TYPE: PRT
<213> ORGANISM: Escherichia coli
<220> FEATURE:
<223> OTHER INFORMATION: alpha peptide (wildtype)

<400> SEQUENCE: 10

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg
    50

<210> SEQ ID NO 11
<211> LENGTH: 52
<212> TYPE: PRT
<213> ORGANISM: Escherichia coli
<220> FEATURE:
<223> OTHER INFORMATION: alpha peptide (N39Q)

<400> SEQUENCE: 11

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Gln Ser Glu Glu Ala Arg Thr Asp Arg Pro
        35                  40                  45

Ser Gln Gln Leu
    50

<210> SEQ ID NO 12
<211> LENGTH: 52
<212> TYPE: PRT
<213> ORGANISM: Escherichia coli
<220> FEATURE:
<223> OTHER INFORMATION: alpha peptide (E41D)

<400> SEQUENCE: 12

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

```
Pro Phe Ala Ser Trp Arg Asn Ser Asp Glu Ala Arg Thr Asp Arg Pro
        35                  40                  45

Ser Gln Gln Leu
    50
```

DETECTION OF PROTEIN TRANSLOCATION BY BETA-GALACTOSIDASE REPORTER FRAGMENT COMPLEMENTATION

CROSS-REFERENCE TO RELATED APPLICATIONS

This application claims the benefit of U.S. Provisional Patent Application No. 60/572,635, filed May 18, 2004, the entire contents of which are incorporated herein by reference.

GOVERNMENT RIGHTS

This invention was made with Government support under contracts AG009521, AG020961, HL065572, & HD018179 awarded by the National Institutes of Health. The Government has certain rights in this invention.

TECHNICAL FIELD

This invention relates generally to the field of molecular biology. More specifically, the invention provides methods and compositions for enzyme-derived reporter systems for detecting molecular locations and, in particular, detecting protein translocation based on reporter group concentration using β-galactosidase.

BACKGROUND OF THE INVENTION

Living cells are exposed to a variety of signals from their micro- and macro-environment. Signals are detected by receptors present on the cell surface and are then processed and transduced by biochemical cascades known as intracellular signaling pathways. Signal transduction through intracellular space is a key part of cell communication and response and often involves the movement—or translocation—of signaling proteins from one position to another within the cell. Novel methods for monitoring specific modulation of intracellular pathways in living cells could provide new opportunities in drug discovery, functional genomics, toxicology, etc.

Several disease states can be attributed to altered activity of individual signaling components, such as protein kinases, protein phosphatases, transcription factors, etc. These signaling components are attractive as targets for therapeutic intervention. Protein kinases and phosphatases are well described components of several intracellular signaling pathways. Although the involvement of protein kinases in cellular signaling have been studied extensively, detailed knowledge of signaling-related translocation events needs convenient technology for its study.

Phosphorylation mediated by protein kinases is balanced by phosphatase activity. Translocation is observed within the family of phosphatases, and is likely to be indicative of phosphatase activity. See, e.g., Cossette et al., *Exp. Cell Res.*, 223:459-66 (1996). Protein kinases often show a specific intracellular distribution before, during and after activation and monitoring the translocation processes of individual protein kinases or subunits thereof is thus likely to be indicative of their functional activity. Connection between translocation and catalytic activation has been shown for protein kinases like protein kinase C, cAMP-dependent protein kinase and mitogen-activated-protein kinase Erk-1. See, e.g., Debernardi et al:, *Proc. Natl. Acad. Sci. USA*, 93:4577-82 (1996); Sano et al., *Brain Res.*, 688:213-18 (1995).

Commonly used methods of detection of intracellular localization of protein kinases and phosphatases include immunoprecipitation, Western blots and immunocytochemistry. Translocation indicative of protein kinase C (PKC) activation has been monitored using different approaches such as immunocytochemistry where the localization of individual isoforms are detected following permeabilization of the cells; tagging all PKC isoforms with a fluorescent-label; chemical tagging of PKC with the fluorophore Cy3 and genetic tagging of PKCα and of PKCγ and PKCε. See, e.g., Khalil et al., *Am. Physiolog. Society*, 263:C714 (1992); Godson et al., *Biochim. et Biophys. Acta*, 1313:69-71 (1996); Bastiaens et al., *Proc. Natl. Acad. Sci. USA*, 93:8407-612 (1996); Wagner et al., *Exp. Cell Res.*, 258:204-14 (2000); Sakai et al., *Soc. Neurosci.*, 22:371, Abstract 150.1 (1996).

Steroid receptors are hormone-dependent activators of gene expression. Steroid receptors mediate the action of steroid hormones (e.g., glucocorticoids, estrogens, progestins, testosterone, mineralocorticoids and 1,25-dihydroxycholecalciferol) in human tissues. After activation with the cognate ligand, receptors bind to chromatin in the nucleus and modulate the activity of target cellular genes. It is generally accepted that the unliganded glucocorticoid receptor (GR) resides in the cytoplasm, and that hormone activation leads both to nuclear accumulation and gene activation. See, e.g., GASC ET AL., STEROID HORMONE RECEPTORS: THEIR INTRACELLULAR LOCALISATION 233-50 (Clark, C.R., ed. Ellis Horwood Ltd. 1987; Beato, *Cell*, 56:335-44 (1989); Carson-Jurica et al., *Endocr. Rev.* 11:201-20 (1990); GRONEMEYER, STEROID HORMONE ACTION 94-117 (Parker, M. G., ed. Oxford University Press 1993); Tsai et al. *Annu. Rev. Biochem.* 63:451-86 (1994); Akner et al., *J. Steroid Biochem. Mol. Biol.* 52:1-16 (1995). However, the mechanisms involved in nuclear translocation and targeting of steroid receptors to regulatory sites in chromatin have been poorly understood. Green Fluorescent Protein has been used in an assay for the detection of translocation of the glucocorticoid receptor. See, e.g., Carey et al., *Cell Biol.*, 133:985-96 (1996). Methods involving tagging a protein target with a luminophore (such as a fluorescent protein like GFP), expressing the luminophore-fusion protein in stably transfected cell lines, and quantifying the target movement in response to pharmacological stimuli by imaging is the subject of patents such as U.S. Pat. No. 6,518,021; EP 0986753B1; U.S. Pat. No. 6,172,188, and EP 0851874.

Directed protein movement in response to external stimuli is a mechanism employed by eukaryotic signal transduction pathways. Perhaps one of the best-studied in vivo signal transduction pathways is the NF-κB pathway, a convergent pathway for a number of different stimuli that impact the cell. Ligand binding and other stimulatory events at the cell surface trigger activation of the cascade that results in the eventual translocation of NF-κB from the cytoplasm to the nucleus. Proteins that are resident along a pathway offer a potential therapeutic targeting opportunity. Current technologies to track these events are limited to biochemical fractionation or fusion to fluorescent proteins.

Proteins have been labeled with fluorescent tags to detect their localization and conformational changes both in vitro and in intact cells. Such labeling is essential both for immunofluorescence and for fluorescence analog cytochemistry, in which the biochemistry and trafficking of proteins are monitored after microinjection into living cells. See, e.g., Wang et al., eds. METHODS CELL BIOL. 29 (1989). Traditionally, fluorescence labeling is done by purifying proteins and then covalently conjugating them to reactive derivatives of organic fluorophores. However, the stoichiometry and locations of dye attachment are often difficult to control, and careful repurification of the proteins is usually necessary.

Biochemical methods are often the most sensitive and quantitative however they are limited by their ability to discern subcellular structures without contamination from other organelles. In addition, the number of manipulations involved in preparing the samples makes these methods cumbersome and prone to high variability. The use of fluorescent proteins to track protein movement has positively impacted the scope and detail with which translocation events can be monitored. However the large amounts of protein necessary for efficient imaging make these experiments difficult to perform with toxic proteins and the supra-physiological levels of target protein can affect the quality of the data obtained. Further, the cell to cell variation is high, coupled to moderately low signal to noise ratios, making the assays more qualitative than quantitative.

Enzyme fragment complementation with beta-galactosidase (β-gal) was first shown in prokaryotes. See, e.g., Ullman et al., *J. Mol. Biol.* 24:339-43 (1967); Ullman et al., *J. Mol. Biol* 32:1-13 (1968); Ullmanetal., *J. Mol. Biol.* 12:918-23 (1965). Assays based on the complementation of enzyme fragments fused to interacting proteins that regenerate enzymatic activity upon dimerization are particularly well suited to monitoring inducible protein interactions. Reviewed in Rossi et al., *Trends Cell Biol.* 10:1 19-22 (2000). These systems have important advantages including low level expression of the test proteins, generation of signal as a direct result of the interaction, and enzymatic amplification. As a result, they are highly sensitive and physiologically relevant assays. See, e.g., Blakely et al., *Nat. Biotechnol.* 18:218-22 (2000). Additionally, assays based on enzyme complementation can be performed in any cell type of interest or in diverse cellular compartments such as the nucleus, secretory vesicles or plasma membrane. The β-galactosidase complementation system of U.S. Pat. No. 6,342,345 and as described in the literature enzymatically amplifies of the signal and can be used to monitor interactions in live cells in real-time. See, e.g., Rossi et al., *Proc. Natl. Acad. Sci. USA* 94:8405-10 (1997); Blakely et al., *Nat. Biotechnol.* 18:218-22 (2000).

Protein translocation is essential for mammalian cells to effect cellular responses, and convey information intracellularly. The use of GFP fusion proteins to track protein movement has revolutionized the ability to gather data regarding these actions and has been particularly useful in studying real-time kinetics of protein movement. However the difficulties associated with quantification of these events, such as small increases in fluorescence, high cell to cell variability, and the necessity for high expression levels of the fusion protein, prohibit its use in certain applications and limit the data to mainly qualitative measurements.

Therefore, what is desired is an assay combining both the localization aspects of fluorescence or luminescence-based assays, and the sensitivity and quantitative aspects of biochemical assays.

BRIEF SUMMARY OF THE INVENTION

Precise and accurate monitoring of protein translocation permits screening for and understanding the interplay key components of biologically relevant cellular signaling pathways. Moreover, such assays provide a means for screening and identifying modulators of protein translocation events that may be useful in the diagnosis, treatment, or prevention of disorders and diseases that can be impacted through protein translocation events. Enzymatic assays confer several advantages in monitoring protein translocation events including signal amplification and a wide variety of substrates for in vivo and in vitro detection. Provided herein is a novel assay system for monitoring protein translocation based on enzymatic complementation.

In one aspect, provided herein is a method to assess the local concentration of a compound, comprising: (a) providing a first reporter component, wherein said first reporter component is coupled to a first compound of interest; (b) providing a second reporter component capable of forming an active complex with said first reporter component to generate a detectable signal, wherein said second reporter component is situated at a site of interest; (c) forming said active complex, wherein the formation results from the association of said first reporter component with said second reporter component when both components are present at said site of interest; and (d) detecting a signal produced by said active complex that is measurably different from the signal generated when said compound does not localize to said site of interest, whereby the differences in said signal reflect the local concentration of said compound at said site of interest. In a specific embodiment, the reporter is a low affinity reporter.

In some embodiments, the compound of interest is a protein or biologically active fragment thereof.

The site of interest can be within a cell. In other words, in situ detection of protein translocation events can be monitored in real time. In some embodiments, the site of interest is the nucleus, cytoplasm, or membrane of said cell. Such sites include, but are not limited to endosome, mitochondria, golgi, nuclear membrane, nucleolus, ER, actin or microtubule cytoskeleton, lysosome, PML bodies, chromatin, P bodies, plasma membrane (exterior and interior), axon, dendrite, and filopodia.

The association of the first reporter component and the second reporter component can be mediated by proximity of the reporter components to one another. In some embodiments, the second reporter component is coupled to a second compound of interest. In this case, the association of the first reporter component and the second reporter component can be mediated by the binding of the first compound of interest to the second compound of interest. Exemplary first and second compounds of interest are a ligand-receptor pair, components of a multimeric receptor, or components of a multimeric protein complex. In some cases, the association of the first reporter component and the second receptor component is mediated by the affinity of the first compound of interest to the second compound of interest in the presence of a third compound of interest. In a particular embodiment, the binding affinity of the first compound of interest for second compound of interest is greater than the binding affinity of the first and second reporter components for each other. The first and second compounds of interest can be proteins. In some instances, the third compound of interest is a protein.

Typically, the generation of the detectable signal does not rely on the transcriptional activation of a reporter construct. For example, the formation of the active complex between the first and second reporter components generates a chromogenic, fluorogenic, enzymatic, or other optically detectable signal without requiring the transcriptional activation of a reporter gene construct. The signal can be detected by any suitable method such as flow cytometric analysis or luminescence assessment.

In some embodiments, the active complex is an enzymatic complex such as, for example, β-galactosidase. When the enzyme is β-galactosidase, the first reporter component is a peptide of β-galactosidase comprising amino acids 5-51 of β-galactosidase. In some embodiments, the first reporter component comprises a H31R mutation. Specifically provided herein is a first reporter component which is SEQ ID NO: 1, SEQ ID NO: 2, SEQ ID NO: 3, SEQ ID NO: 4, SEQ ID NO: 5, SEQ ID NO: 6, SEQ ID NO:8, SEQ ID NO:9, SEQ ID NO: 10, or SEQ ID NO: 11. When the enzyme is β-galactosidase, the second reporter component can be a fragment of β-galactosidase with at least one mutation or deletion in the region of amino acid 1 to 56. In a specific embodiment, the second reporter component is SEQ ID NO: 7.

The active enzyme complex used in these methods can be any enzyme including, but limited to β-lactamase or DHFR. In some embodiments, the first and second reporter components are each fluorescent proteins and the detectable signal results from fluorescence resonance energy transfer (FRET). Luminescent proteins may also be employed. Thus, the first reporter component is a luminescent protein and the second reporter component is a fluorescent proteins and the detectable signal results from bioluminescence resonance energy transfer (BRET). In some embodiments, the reporters are low-affinity. Any suitable fluorescent protein can be used including, but not limited to green, red, cyan and yellow fluorescent proteins. In one example, the luminescent protein is a Renilla luciferase or a firefly luciferase.

In some embodiments, the first reporter component, the second reporter component, or both can be coupled to the protein of interest as a fusion polypeptide. The second reporter component can be coupled to a peptide that localizes in a membrane or an intracellular compartment. The peptide can be a triplet SV40 nuclear localization signal.

The first reporter component and second reporter can be provided to the cell by any suitable means. In some embodiments, the reporter components are provided in expression vector. The expression vectors can be viral vectors such as retroviral vectors.

The localization of the compound assessed by the methods provided herein can be inducible, for example, by an intracellular signal cascade. Such localization can be induced in response to a hormone, cytokine, pharmaceutical agent, external stressor, or some combination thereof.

In some embodiments, the localization assessed is the movement of the first reporter component away from the site of interest.

In another aspect, provided herein is a method to assess intracellular protein translocation, comprising: (a) providing a first reporter component to a cell, wherein said first reporter component is coupled to a protein of interest; (b) providing a second reporter component capable of forming an active complex with the first low-affinity reporter component to generate a detectable signal, to said cell, wherein said second reporter component is localized to a specific subcellular region; (c) forming said active complex, wherein the formation is mediated by the binding of the first low affinity reporter component to the second reporter component when both components are localized to said specific subcellular region; and (d) detecting a signal produced by said active complex that is measurably different from the signal generated when said protein of interest does not localize to said specific subcellular region.

In yet another aspect, provided herein is a method for a no-wash ELISA assay for detecting a compound in a sample, comprising: (a) immobilizing a first low-affinity reporter component and a first agent that binds said compound on a support; (b) contacting said support with a solution comprising said compound; (c) adding a second low affinity receptor component coupled to a second agent that binds said compound; (d) forming an active complex of said first and second reporter components, wherein said complex is mediated by binding of said second agent to said compound bound to said first agent; and (e) detecting a signal that is measurably different from a signal generated when said compound is not bound by said first or second agent.

In some embodiments, the second agent is an antibody or biologically active fragment thereof specific for the compound. Sometimes, the first agent is also an antibody or biologically active fragment thereof.

Typically, the formation of the active complex between the first and second reporter components generates a chromogenic, fluorogenic, enzymatic, or other optically detectable signal. Sometimes, the active complex is an enzymatic complex. For example, the active complex can be β-galactosidase. When the enzyme is β-galactosidase, the first reporter component can be a fragment of β-galactosidase lacking with at least one mutation or deletion in the region of amino acid 11 to 44. In a specific embodiment, the first reporter component is SEQ ID NO: 7. When the active complex is β-galactosidase, the second reporter component can be a peptide of β-galactosidase comprising amino acids 5-51 of β-galactosidase. In some embodiments, the second reporter component comprises a H31R mutation. Specifically provided herein is a second reporter component is SEQ ID NO: 2, SEQ ID NO: 3, SEQ ID NO: 4, SEQ ID NO: 5, or SEQ ID NO:6. Alternatively, the α peptide may be the first reporter component and the ω peptide the second reporter component.

Any suitable support can be employed in this method. For example, the support can be glass, silica, plastic, nylon or nitrocellulose. In a specific example, the support is ELISA plate, bead or particle.

Sometimes, the compound is a protein. In a specific embodiment, the compound is vitellogenin. In some embodiments, the compound is a pollutant. Exemplary pollutants include PCB, flucythrinate, and organochlorine compounds.

In one aspect, provided herein is a no-wash ELISA kit to detect the presence of a compound comprising: (a) a first reporter component; (b) a first agent that specifically binds said compound; (c) a second agent that specifically binds said compound; (d) a support; and (e) optionally, instructions for use. In some embodiments, the reporter components are low affinity.

In another aspect, provided herein is a nucleic acid sequence comprising SEQ ID NO: 1, SEQ ID NO: 2, SEQ ID NO: 3, SEQ ID NO: 4, SEQ ID NO: 5, SEQ ID NO: 6, SEQ ID NO:8, or SEQ ID NO:9, a vector comprising the nucleic acid sequence, and a cell comprising the nucleic acid sequence or the vector. Also provided herein is a polypeptide encoded by the nucleic acid sequences provided herein. Specifically, provided herein is a polypeptide comprising the polypeptide encoded by SEQ ID NO: 1, SEQ ID NO: 2, SEQ ID NO: 3, SEQ ID NO: 4, SEQ ID NO: 5, SEQ ID NO: 6, SEQ ID NO:8, or SEQ ID NO:9.

In yet another aspect, provided herein is a kit for assessing the local concentration of a compound comprising: (a) a nucleic acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO:8, or SEQ ID NO:9, or vector comprising said sequence; (b) a nucleic acid sequence as set for in SEQ ID NO: 7 or vector comprising said sequence; and (c) optionally, instructions for use of said nucleic acid sequences.

In another aspect, provided herein is a method for identifying a modulator of protein translocation, comprising: (a) providing a first reporter component to a cell, wherein said first reporter component is coupled to a protein of interest; (b) providing a second reporter component capable of forming an active complex with said first reporter component to generate a detectable signal, to said cell, wherein said second reporter component is localized to a specific subcellular region; (c) providing a signal to said cell that induces the translocation of one of said reporter components, wherein the translocation results in the formation of said active complex via the binding of said first reporter component to said second reporter component when both components are localized to said specific subcellular region; (d) contacting said cell with a candidate modulator compound; and (d) detecting a signal produced by said active complex in the presence of said candidate compound relative to that signal produced by said active complex in the absence of said candidate modulator compound, whereby said candidate compound is identified as said modulator compound whose presence results in a measurably different signal from the signal generated in the absence of said candidate modulator compound.

Further provided herein is a method of sorting or for detecting at least one live cell where protein translocation is induced or modified in a cell mixture, comprising separating the cells of the methods disclosed herein according to the degree they are generate said signal from said first and second reporter components, using flow cytometric cell analysis.

Also provided herein is a method to visualize intracellular translocation in real time comprising detecting the signal generated in the cells comprising the receptor components disclosed herein using confocal microscopy.

In one embodiment, a reporter system is provided for detecting a location of a molecule on a substrate, the system comprising: a first low-affinity reporter component coupled to a putative binding moiety localized on the substrate; and at least a second low-affinity reporter component coupled to the molecule and capable of forming an active complex with the first low-affinity reporter component to generate a detectable signal, wherein the formation of the active complex is mediated by binding of the molecule to the putative binding moiety, and further wherein the detectable signal is measurably different from a signal generated when first putative binding moiety is not localized on a substrate.

In another embodiment, a reporter system for detecting a location of a molecule on a substrate, the system comprising: a first low-affinity reporter component and a putative binding moiety immobilized adjacent to each other on the substrate; and at least a second low-affinity reporter component coupled to the molecule and capable of forming an active complex with the first low-affinity reporter component to generate a detectable signal, wherein the formation of the active complex is mediated by binding of the molecule to the putative binding moiety, and further wherein the detectable signal is measurably different from a signal generated when first putative binding moiety is not localized on a substrate.

The invention provides a method for detecting localization of a molecule, said method comprising: (a) providing a first low-affinity reporter component coupled to a putative binding moiety localized on the substrate; (b) providing a second low-affinity reporter component coupled to the molecule and capable of forming an active complex with the first low-affinity reporter component to generate a detectable signal; (c) forming the active complex mediated by binding of the molecule to the putative binding moiety; and (d) detecting a signal that is measurably different from a signal generated when first putative binding moiety is not localized on a substrate. In one embodiment, the method provides a first low-affinity reporter component and a putative binding moiety immobilized adjacent to each other on the substrate instead.

In some embodiments, wherein the first and second low-affinity reporter components are each inactive, complementary fragments of an enzyme and the detectable signal results from complementation to generate an enzymatic activity. The enzyme may be β-galactosidase. In a preferred embodiment, first component is an omega-fragment of β-galactosidase and the second component is an alpha-peptide of β-galactosidase comprising a H31R mutation. In other embodiments, the enzyme is β-lactamase, or DHFR.

In one embodiment, the first and second low-affinity reporter components interact to provide a detectable signal resulting from a ras-dependent reporter gene derived from a Ras Recruitment System (RRS) or a Sos Recruitment System (SRS).

In one embodiment, the first and second low-affinity reporter components are each fluorescent proteins and the detectable signal results from fluorescence resonance energy transfer (FRET). In one embodiment, the first reporter component is a luminescent protein and the second low-affinity reporter component is a fluorescent proteins and the detectable signal results from bioluminescence resonance energy transfer (BRET). In some embodiments, the fluorescent protein is selected from the group consisting of green, red, cyan and yellow fluorescent proteins; and the luminescent protein is a Renella luciferase or a firefly luciferase.

In some embodiments, the formation of an active complex between the first and second reporter components generates a chromogenic, fluorogenic, enzymatic, or other optically detectable signal.

In some embodiments, the molecule is a ligand; the putative binding moiety is a receptor; and the substrate is membrane of a cell such as a nuclear membrane or a plasma membrane. In some embodiments, the ligand is translocated to the membrane in a signal transduction process, or a hormonal treatment, or in response to cellular stress. In some embodiments, the location of the ligand is detected by flow cytometry.

The invention also provides a method for no-wash ELISA assay for detecting an antigen, the method comprising: (a) immobilizing a first low-affinity reporter component and a first antibody to a first epitope of the antigen adjacent to each other on a microwell plate; (b) contacting the microwell with a sample suspected of containing the antigen; (c) adding a second low-affinity reporter component coupled to a second antibody to a second epitope on the antigen; (d) forming an active complex mediated by binding of the first and second antibodies to the antigen; and (e) detecting a signal that is measurably different from a signal generated when the antigen is not bound to the first antibody on the microwell.

One embodiment of the invention provides a method for no-wash ELISA assay for detecting a pollutant in a tissue sample, the method comprising: (a) immobilizing a first low-affinity reporter component and the tissue sample adjacent to each other on a microwell plate; (b) contacting the microwell with a solution comprising an antibody to the pollutant antigen wherein a second low-affinity reporter component is coupled to the antibody; (d) forming an active complex of the first and second low-affinity reporter components mediated by binding of the antibody to the pollutant antigen; and (e) detecting a signal that is measurably different from a signal generated when the pollutant antigen is not bound to the antibody on the microwell. The pollutant may be selected from the group consisting of PCB, flucythrinate and organochlorine compounds; or the pollutant is detected by assaying vitellogenin as the antigen.

BRIEF DESCRIPTION OF THE FIGURES

In FIG. 1A, the right panel shows the first 137 amino acids of β-galactosidase fused to the C-terminus of GFP and serially truncated. These constructs were co-expressed with the ω in C2C12 cells and assayed for β-galactosidase The left panel of FIG. 1A shows amino acids 1-51 of β-galactosidase fused to the N-terminus of GFP, serially truncated, then co-expressed with the ω fragment. The minimal fragment was defined by combining the last C (47R) and N (5D) terminal truncations then fused to the N and C terminus of GFP. These fusions were co-expressed with the ω and assayed for enzyme activity.

FIG. 2A illustrates the design of the nuclear translocation assay. In the left panel, the ω fragment is localized to the nucleus with a nuclear localization signal (NLS) and the cytosolic protein of interest is fused to the minimal α peptide. Upon stimulation, the α fusion moves to the nucleus and complements the ω, increasing β-galactosidase activity. In the right panel, the ω fragment is tethered to the plasma membrane using the extracellular and transmembrane regions of EGFR. The cytosolic α-fusion complements spontaneously until stimulation when it translocates to the nucleus which results in a loss of enzyme activity.

FIG. 2B shows a nuclear translocation test system comprising a fusion protein consisting of the mitogen activated protein kinase kinase (MAPKK or MEK) segment that acts as a nuclear export signal (NES) fused to GFP, the α peptide and a triplet SV40 NLS. At steady state the protein is cytosolic, left panel. In the presence of leptomycin B (right panel) the protein becomes nuclear.

FIG. 2C shows a gain of signal assay in the left panel. The NES-GFP-α-NLS protein was coexpressed with the ω-NLS and addition of leptomycin B for 2.5 hours results in a gain of β-galactosidase activity. A loss of signal assay is shown in the right panel. Transduction of cells expressing the tEGFR-ω fusion with the NES-GFP-α-NLS construct results in a loss of β-galactosidase activity in the presence of leptomycin B.

FIG. 3A shows a time course of cells expressing the GR-α fusion and either the ω-NLS (Left) or tEGFR-ω (right) were assayed for β-galactosidase activity after treatment with 1 μM dexamethasone for the indicated times.

FIG. 3B shows dose versus time with cell lines shown in FIG. 3A treated with varying concentrations of dexamethasone and assayed over time.

FIG. 3C shows protein localization monitored by flow cytometry. The GR-α cell lines were treated with 1 μM dexamethasone (red) for three hours, then stained with the fluorescent β-galactosidase DDAO substrate and analyzed by flow cytometry. Following dexamethasone treatment, the treated cells (red) demonstrated staining for the fluorescent β-galactosidase substrate.

FIG. 4A shows the crystal structure of wild type β-galactosidase with the α peptide pictured in yellow (light colored) and the mutations indicated.

FIG. 4B shows mutations made in the α-peptide fused to the C-terminus of GFP. These constructs were transduced into cells expressing the tEGFR-ω and assayed for β-galactosidase activity.

FIG. 4C shows a schematic of the membrane translocation assay wherein the ω fragment is tethered to the plasma membrane using the extracellular and transmembrane regions of the EGFR. Four of the mutants were fused to the C1A domain of PKCγ and coexpressed with the tEGRF. Their responses to 1 μM PMA for 20 minutes are expressed as a fold induction over background.

FIG. 4D shows the H31R mutant that showed the highest fold induction, treated with varying levels of PMA and then assayed for β-galactosidase activity.

FIG. 4E shows single cell analysis by flow cytometry in live cells using the DDAO fluorescent substrate.

FIG. 5 shows translocation of the AKT PH domain monitored by β-galactosidase complementation.

FIG. 5A shows the AKT-GFP-α fusion protein transduced into 3T3 cells expressing the tEGFR-ω fusion. The cells were treated with 50 ng/ml PDGF, insulin, or sorbitol for the indicated times and assayed for β-galactosidase activity using the luminescent substrate.

FIG. 5B shows sequential stimulation of cells used in FIG. 5A with insulin, PDGF and Sorbitol followed by assay for β-galactosidase activity.

DETAILED DESCRIPTION OF THE INVENTION

Figure 1:
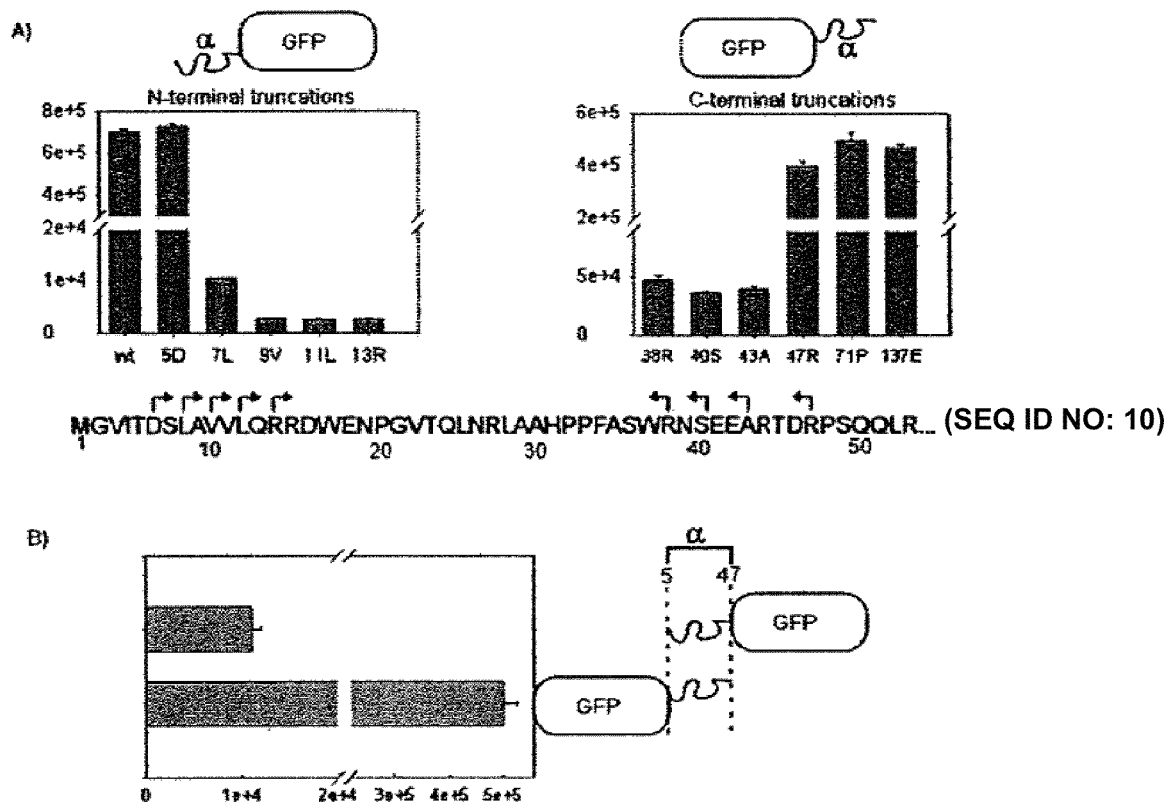
FIG. 1 schematically depicts a design of the minimal fragment.

Control of protein localization represents one of the fundamental mechanisms employed by cells to manage protein-protein interaction and to precisely generate cellular signals. Alterations in protein localization results in modification of basic cellular activation pathways. For example, a change in the localization of a specific protein may induce or abrogate the activation of the cellular activation pathway involving that protein. Current technologies to monitor protein localization are currently limited to biochemical fractionation or fusion to fluorescent proteins. See, e.g., Lever et al., (1980) and Tsien et al., (1998). While some of the biochemical methods demonstrate good sensitivity, these methods are limited by their ability to discern only a limited number of subcellular structures without contamination from other organelles. Moreover, the number of manipulations involved in preparing these samples makes these methods cumbersome and introduces high variability. Fluorescent proteins increased the scope and detail for monitoring protein translocation, but remains limited by the large quantity of proteins necessary for efficient imaging. See, e.g., Balla et al., (2002). The quantity requirement can diminish the quality of the data, reduces the method's sensitivity, and limits the ability to perform such experiments with toxic proteins. The high cell-to-cell variation coupled to a moderately low signal to noise ratio renders these methods more qualitative than quantitative. Thus, an assay that combines the localization aspects of fluorescent proteins such as GFP with the sensitivity of biochemical assays increases the quantitative power and sensitivity of the assay without a significant protein quantity requirement.

Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

The term "active complex" refers to an enzyme or other protein that is capable of generating a detectable signal in the absence of transcriptional activation of a reporter construct. Typically, active complexes are enzymes. Such enzymes are capable of catalyzing the production of a detectable product directly or indirectly and may be modified by recombinant techniques to improve their detectable product production.

As used herein, the term "antibody" refers to any form of antibody or fragment thereof that specifically binds then antigen of interest. Thus, it is used in the broadest sense and specifically covers monoclonal antibodies (including full length monoclonal antibodies), polyclonal antibodies, multi-specific antibodies (e.g., bispecific antibodies), and antibody fragments so long as they specifically bind the target of interest. Any specific antibody can be used in the methods and compositions provided herein. Thus, the term "antibody" encompasses a molecule comprising at least one variable region from a light chain immunoglobulin molecule and at least one variable region from a heavy chain molecule that in combination form a specific binding site for the target antigen. As used herein, the term "specific" refers to the selective binding of the antibody to the target antigen epitope such that it does not bind irrelevant or unrelated epitopes.

As used herein, a "detectable signal" refers to any detectable signal which occurs upon the association of the reporter components or via the interaction of the associated components with another substance, e.g., a substrate. Such detectable signals include, but are not limited to a chromogenic, fluorescent, phosphorescent, luminescent, or chemiluminescent signal.

As used herein, the term "cell" refers to any cell enclosed by a plasma or cell membrane. Preferably, the cell is a mammalian cell. The cell can be human or nonhuman. The cell can be freshly isolated (i.e., primary) or derived from a short term- or long term-established cell line. Exemplary cells include embryonic, neonatal or adult cells, transformed cells (e.g., spontaneously- or virally-transformed), neoplastic, and malignant cells. These include, but are not limited to fibroblasts, macrophages, myoblasts, osteoblasts, osteoclasts, hematopoietic cells, neurons, glial cells, primary B- and T-cells, B- and T-cell lines, chondrocytes, keratinocytes, adipocytes, hepatocytes, monocytes, endothelial cells, smooth muscle cells, and pericytes. In some embodiments, the cells have been engineered using recombinant technology to express one or more exogenous proteins or to "knock out" expression of one or more endogenous proteins. For example, a mammalian cell line may be engineered to express (or overexpress) a receptor protein.

As used herein, the term "expression system" refers to any suitable exogenous system for expressing the receptor components in the cell. For example, exogenous expression of receptor components by a cell as provided herein can result from the introduction of the nucleic acid sequences encoding the receptor component or a fusion protein comprising a receptor component in an expression vector. As used herein, the term "fusion protein" refers to a reporter component that is fused to a heterologous protein or protein fragment using recombinant technology.

The term "reporter component" refers to a member of a complex of two or more subunits that lacks the ability to generate a detectable signal, but is capable to generating a detectable signal when associated with one or more other members of the active complex. Thus, typically the receptor components used in a cell complement one another such that at least one biological activity can be detected.

As used herein, the terms "protein", "polypeptide", and "peptide" are used interchangeably herein to refer to polymers of amino acids of any length. The polymer may be linear or branched, it may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

Unless otherwise indicated, the practice of the present invention will employ conventional techniques of molecular biology, biochemistry, microbiology, recombinant DNA, nucleic acid hybridization, genetics, immunology, embryology and oncology which are within the skill of the art. Such techniques are explained fully in the literature. See, e.g., MOLECULAR CLONING: A LABORATORY MANUAL 2d Ed (Maniatis et al., eds. Cold Spring Harbor Laboratory Press 1989); CURRENT PROTOCOLS IN MOLECULAR BIOLOGY (Ausubel, et al., John Wiley & Sons 1987-current edition).

For clarity of disclosure, and not by way of limitation, the detailed description of the invention is divided into the subsections that follow. The examples that follow are included for illustrative purposes only and are not intended to limit the scope of the invention.

Translocation Detection Methods

The compositions and method provided herein allow for rapid, quantitative, in situ monitoring of protein translocation using a protein component complementation assay system where two inactive components of a reporter protein exhibit a detectable signal when the components associate with one another, indicating that the protein(s) being monitored are in the same location.

The methods provided herein offer several advantages over either fluorescent protein or biochemical assays. First, a wide variety of substrates may be employed for in situ analysis, allowing the methods to be used in histological, flow cytometry, and high-throughput screening applications. Second, the small size of the α peptide reduces artifacts and eliminates limitations resulting from the use of large complementing peptides in assays previously described. The smaller size peptide is much less likely to interfere with normal translocation events. Moreover, because both subunits are necessary for complementation, efficient localization of the ω to a specific cellular location ensures signal generation solely from this region. The assay can be performed in any cell type using the smaller peptide method, including non-adherent cells that are difficult to image using fluorescent proteins. Another advantage lies in the ability of the complemented enzyme to process multiple molecules of substrate, amplifying the signal obtained from the translocation event. The amplification permits the detection of fewer numbers of molecules than microscopy-based assays, thereby allowing the studied protein to be expressed at physiologically relevant concentrations. Such an assay is ideal for toxic proteins or those localized by a binding partner that is not exogenously expressed. A further advantage of this amplification is to provide a high signal to noise ratio. The robust signal coupled to the low sample variability, generates a highly sensitive and quantitative assay for protein translocation that is applicable to all cell types in a high-throughput screening fornat.

In one aspect, provided herein is a method to assess the local concentration of a compound, comprising: (a) providing a first reporter component, wherein said first reporter component is coupled to a first compound of interest; (b) providing a second reporter component capable of forming an active complex with said first reporter component to generate a detectable signal, wherein said second reporter component is situated at a site of interest; (c) forming said active complex, wherein the formation results from the association of said first reporter component with said second reporter component when both components are present at said site of interest; and (d) detecting a signal produced by said active complex that is measurably different from the signal generated when said compound does not localize to said site of interest, whereby the differences in said signal reflect the local concentration of said compound at said site of interest.

In another aspect, provided herein is a method to assess intracellular protein translocation, comprising: (a) providing a first low affinity reporter component to a cell, wherein said first reporter component is coupled to a protein of interest; (b) providing a second low affinity reporter component capable of forming an active complex with the first low-affinity reporter component to generate a detectable signal, to said cell, wherein said second reporter component is localized to a specific subcellular region; (c) forming said active complex, wherein the formation is mediated by the binding of the first low affinity reporter component to the second reporter component when both components are localized to said specific subcellular region; and (d) detecting a signal produced by said active complex that is measurably different from the signal generated when said protein of interest does not localize to said specific subcellular region.

Any suitable reporter can be employed in the claimed methods. In a specific embodiment, the reporter is a protein. The reporter components represent a complementary portion of the reporter that alone is inactive or devoid of signal-emitting activity. However, when the reporter components interact with one another, the reporter components interact to generate a detectable signal. The interaction of the complementary reporter components can be mediated by increased localization at a particular site, exceeding a critical concentration, multimerization, proximity, and the like.

For example, the fragments of the reporter enzyme are made such that there is one large fragment being at least 80%, sometimes at least 90% or 95% of the full length parental enzyme, and a smaller fragment that encodes less than 20% of the native (i.e., non-fragmented) enzyme necessary to complement the larger fragment to result in detectable enzymatic activity. The larger fragment is of sufficient length to be properly folded and forms the three dimensional or tertiary structure resembling the native enzyme. In some embodiments, complementation may be achieved with more than 2 enzyme fragments or may include additional interacting proteins, i.e., a third protein or other components that facilitate the complementation of the two fragments. The tertiary structure of the large fragment can be determined in solution in the absence of the complementing fragment using any suitable method. Such methods include 1) binding by antibodies that are specific for the folded state of the enzyme; 2) ability to bind substrate; or 3) similar pattern of accessibility of amino acids exposed to reactive compounds (e.g., solvent and the like) by comparison with the parental enzyme. A pattern of accessibility means that the amino acids on the outside of the protein react with certain reagents first while the ones on the inside are protected using routine methods.

In one embodiment, the reporter components are low affinity components. In other words, the design of the reporter components reduces affinity of the components for one another such that their interaction can be increased by increasing the concentration of either fragment. Thus, the low affinity components provided herein generate detectable signal that is dependent on the local concentration of each of the fragments. In some embodiments, the interaction is achieved by coupling a first reporter component to a protein of interest while the second reporter component is coupled to a second protein that interacts with the first protein when co-localized with the second protein. The affinity of the components is such that the signal generated when components in solution is detectably less than or undetectable relative to the signal generated when the components are proximal to one another as a result of a translocation event. For example, low affinity components are useful when examining translocation events within the same cellular compartment such as that from the cytosol to the plasma membrane. Because the low affinity components are unable to mediate full complementation, localized increases in concentration drive the generation of detectable enzymatic activity. For example, the necessary increase in concentration can be achieved if one reporter component is localized to the interior of the plasma membrane and the other is fused ot a cytosolic protein. Coexpression of the low affinity reporter components will typically result in a low level of detectable enzymatic activity. However, if the cytosolic fusion protein is induced to translocate to the plasma membrane, then a detectable different amount of enzymatic activity will result because of the greater concentration of the low affinity reporter components. While the total cytosolic concentration of reporter components is the same, the distribution has changed and results in a detectably different signal resulting from the complementing reporter components. Thus, the use of low affinity components permits the detection of movement of proteins within a subcellular compartment.

Any suitable method can be used to design and generate low affinity mutants, including those disclosed herein. For example, deletions, insertions, or point mutations of the primary enzyme sequence of one or both fragments such that mixing of these fragments under the appropriate conditions for that enzyme in solution provides less than 30% of the activity obtained with the parental fragments when mixed in equal amounts in the range of $10^{-3}$ to $10^{-6}$ M, sometimes about 1, 5, 10, 15, 20, or 25% of the enzymatic activity of the native enzyme. Furthermore, increasing the concentration of either of the two fragments by at least 4-fold results in a measurable increase in enzyme activity. Low affinity fragments are thus defined relative to high affinity fragments. In one example, complementation with high affinity fragments occurs at a 1:1 ratio, while complementation with low affinity fragments occurs at a ratio greater than 1:1 of the large to small fragment.

In other embodiments, the reporter components are high affinity components. Any suitable method can be used to design and generate low affinity mutants, including those disclosed herein. High affinity components are generally two fragments of an enzyme with the fragments having sufficiently high affinity such that they can spontaneously bind to each other and reform a fully functional enzyme or enzyme subunit. Typically, at least 5% of enzymatic activity of the native enzyme is achieved when mixed under appropriate conditions in solution, sometimes about 10, 20, 30, 40, 50, 60, 70, 80, 90, 95, 99, or 100% of the enzymatic activity of the native enzyme. Determination of such activity can be performed using routine methods with the concentration at which the complemented enzyme and parental enzyme are compared typically being the same with a range of, e.g., between $10^{-3}$ to $10^{-6}$ M. High affinity components permits monitoring of the presence, absence, or increase of the reporter components as they translocate between subcellular compartments. For example, if one reporter component is localized to a distinct separable cellular compartment such as the nucleus, then the translocation of the second component into the nucleus will result in detectable enzymatic activity, thus permitting the analysis of nucleus translocation. Accordingly, if the amount of high affinity components increases in the nucleus, then the amount of detectable enzymatic activity will increase proportionally. Typically, large increases in the amount of activity are detectable up to a 1:1 reporter component ratio.

Suitable reporters include β-galactosidase, DHFR, β-lactamase, ubiquitin, ras-based recruitment systems (RRS and SOS), G-protein signaling, green fluorescent protein (GFP), fluorescence resonance energy transfer (FRET), bioluminescence resonance energy transfer (BRET), fusion-protein based systems such as yeast two hybrid method, and the like. See, e.g., Remy, et al., *Science* 283:990-93 (1999); Remy, et al., *Proc. Natl. Acad. Sci. USA* 96:5394-99 (1999); U.S. Pat. Nos.: 6,270,964, 6,294,330 and 6,428,951; Wehrman, et al., *Proc. Natl. Acad. Sci. USA* 99:3469-74 (2002); U.S. Patent Appl'n. No. 20030175836; Johnsson, et al., *Proc. Natl. Acad. Sci. USA* 91:10340-44 (1994); U.S. Pat. Nos.: 5,503,977 and 5,585,245; Aronheim, *Methods Mol. Biol.* 250:251-62 (2004); Maroun et al., *Nucleic Acids Res.* 27:e4 (1999); Aronheim, *Nucleic Acids Res.* 25:3373-74 (1997); Ehrhard et al., *Nature Biotechnol.* 18:1075-79 (2000); Remy, et al., *Methods* 32:381-88 (2004); Pollok et al., *Trends Cell Biol.* 9:57-60 (1999); Adams, et al., *Nature* 349:694-97 (1991); Fields, et al., *Nature* 340:245-46 (1989); Ray P. et al., *Proc. Natl. Acad. Sci. USA* 99:3105-10 (1999); Xu et al., *Proc. Natl. Acad. Sci USA* 96:151-56 (1999); Ayoub et al., *J. Biol. Chem.* 277: 21522-28 (2002); Paulmurugan et al., *Cancer Res.* 64:2113-19 (2004).

The reporter component can be coupled to the compound of interest using any suitable method. Thus, the reporter component and one or more compounds are generally linked either directly or via a linker. Typically, the linker is covalent. For example, when the reporter component and the compound are proteins, methods known in the art for linking peptides can be employed. In one preferred embodiment, the reporter component and the compound comprise a fusion protein that includes the reporter component and the compound being assayed. The fusion protein is expressed from an encoding nucleic acid intracellularly. This method of expression is particularly advantageous for analysis of protein translocation.

Any suitable expression system can be used to express the reporter components in situ. Transformation may be achieved using viral vectors, calcium phosphate, DEAE-dextran, electroporation, cationic lipid reagents, or any other convenient technique known in the art. The manner of transformation useful in the present invention are conventional and are exemplified in CURRENT PROTOCOLS IN MOLECULAR BIOLOGY (Ausubel, F. M., et al., eds. 2000). Exogenous expression of the receptor components can be transient, stable, or some combination thereof. Exogenous expression can be enhanced or maximized by co-expression with one or more additional proteins, e.g., HIV rev. Exogenous expression can be achieved using constitutive promoters, e.g., SV40, CMV, and the like, and inducible promoters known in the art. Suitable promoters are those which will function in the cell of interest. In one embodiment, the expression vector is a retroviral vector.

The level of expression of the receptor component is that required to detect the translocation event. One of ordinary skill in the art can determine the required level of expression for translocation detection using assays routinely employed in the art. Generally, the fusion gene constructs are expressed at low levels in situ to facilitate the monitoring of intracellular translocation events in the presence of, e.g., endogenous regulators of protein translocation. Low expression levels reduces and sometimes eliminated artifacts arising from overexpression of such proteins. Low level expression is readily achieved using appropriate promoters, ribosome binding sites and other regulatory elements in expression systems tailored for the specific cell employed. For example, fusion gene constructs can be introduced into vectors in which they lie upstream of an antibiotic resistance gene whose translation is regulated by the Encephalomyocarditis virus internal ribosome entry sequence (IRES), and which contain a mutation in the splice donor/acceptor sequences upstream of the ATG sequence responsible for translational initiation of the fusion gene. This type of construct results in a lower translation efficiency of the first coding sequence in a bicistronic message, but does not affect translation of the second (antibiotic resistance) sequence, which is solely dependent on the IRES.

Also provided herein are vectors or plasmids containing a nucleic acid that encodes for a receptor component or a fusion protein comprising a receptor component. Suitable vectors for use in eukaryotic cells are known in the art and are commercially available or readily prepared by a skilled artisan. Additional vectors can also be found, for example, in CURRENT PROTOCOLS IN MOLECULAR BIOLOGY (Ausubel, F. M., et al., eds. 2000) and SAMBROOK ET AL., ED. MOLECULAR CLONING: A LABORATORY MANUAL 2nd Ed. (1989). In one embodiment, the first reporter component is encoded in a different vector or plasmid than the second reporter component. In another embodiment, the first reporter component is encoded in the same vector or plasmid as the second reporter component. The reporter components expression systems (or constructs) may be introduced into mammalian cells by methods available in the art, including, but not limited to, viral vectors, transformation, co-precipitation, electroporation, neutral or cationic liposome-mediated transfer, microinjection or gene gun. Once the nucleic acid is incorporated into a cell as provided herein, the cell can be maintained under suitable conditions for expression of the reporter components. Generally, the cells are maintained in a suitable buffer and/or growth medium or nutrient source for growth of the cells and expression of the gene product(s).

In some embodiments, the methods provided herein utilize one or more reporter components whose natural affinity for the other reporter component is modified using molecular biology techniques. Modifications includes those made by one or more steps of mutagenesis, truncation, modification, insertion, and the like in the nucleic acid sequence of the reporter component. See, e.g., CURRENT PROTOCOLS IN MOLECULAR BIOLOGY (Ausubel et al., ed. John Wiley & Sons 2003). For example, such modification can be introduced using random mutagenesis, deletion, or directed mutation based on molecular modeling information. In some embodiments, the affinity of the individual reporter components for each other are reduced to a level where significant detectable signal is not generated unless one of the components is localized on a membrane or a solid support. Methods for generating low affinity reporter components include point mutations, insertion of foreign sequences, and deletions of residues either internally or from either terminus. See, e.g., Dunn et al., *Protein Eng.* 2:283-91 (1988); Poussu et al., *Proteins* 54:681-92 (2004). In other words, there is a detectable difference in the signal generated when the two components are brought together in solution versus when at least one component is initially localized on a membrane or immobilized on a support.

Compounds useful in these methods are those whose biological activity involves translocation from location in a cell to another and can be readily coupled to one or more of the reporter components. In some embodiments, the compound is a protein or biologically active fragment thereof. Exemplary proteins include proteins in one or more signal transduction cascades, apoptosis regulation, cell-cycle progression, carcinogenesis, metastasis, transcription and/or its regulation, translation and/or its regulation, proteins that affect cell interactions, cell adhesion molecules (CAMs), ligand-receptor pairs, proteins that participate in the folding of other proteins, and proteins involved in targeting to particular intracellular compartments, such as the Golgi apparatus, endoplasmic reticulum, ribosomes, chloroplasts and mitochondria.

Exemplary proteins that affect intracellular translocation events include, but are not to hormones and cytokines that are involved in signal transduction, such as interferons, chemokines, and hematopoietic growth factors. Some examples include lymphotoxin, tumor necrosis factor, Fas ligand (CD95L) TNF-related apoptosis-inducing ligand (TRAIL), transforming growth factors-α and β (TGF-α and TGF-β), macrophage and granulocyte colony stimulating factors, epidermal growth factor (EGF), nerve growth factor (NGF), platelet-derived growth factor (PDGF), insulin-like growth factors I and II (IGF-I and IGF-II), endorphins, prostaglandins, neurotransmitters, adrenergic receptors, and cholinergic receptors. Other proteins include intracellular enzymes such as protein kinases, phosphatases and synthases. One exemplary enzyme is interleukin-1β converting enzyme (ICE) proteases or caspase 8. Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics. Thus, the method provided herein employs one or more components of the ligands (such as those listed above) and their respective receptors and related signalling components. Specifically, in some embodiments, first and second compounds of interest are a ligand-receptor pair, components of a multimeric receptor, or components of a multimeric protein complex.

Additional interactions that can be studied by the practice of the invention include interactions involved in cell metabolism and cell structure. These include, but are not limited to, interactions that are involved in energy metabolism or which establish or modify the structure of the membranes, cytoplasm, cytoskeleton, organelles, nuclei, nuclear matrix or chromosomes of cells. Interactions among constituents of the extracellular matrix, or between constituents of the extracellular matrix and cells, can also be studied with the methods and compositions of the invention.

Binding of molecules will depend upon factors in solution such as pH, ionic strength, concentration of components of the assay, and temperature. In the binding assays using reporter systems described herein, the binding affinity of the binding moieties should be high enough to permit forced complementation between the reporter subunits. Non-limiting examples of dissociation constants of the binding moieties in an assay solution, such as a buffered system or cell interior, are on the order of less than about $10^{-8}$ M, for example, less than about $10^{-9}$ M, or optionally, between about $10^{-9}$ to $10^{-12}$ M, depending upon the properties of the particular assay system.

Binding between reporter components or between more than one compound of interest can be direct or in the form of a complex with one or more additional binding species, such as charged ions or molecules, ligands or macromolecules. Thus, the presence or absence of functional reporter molecule is detected by the presence or absence of a signal produced by the functional reporter molecule.

In one embodiment, the functional reporter molecule is an enzyme whose activity can be monitored by the appearance of a product of the enzymatically catalyzed reaction (e.g., an increase in detectable signal) or by disappearance of the enzyme substrate (e.g., a decrease in or quenching of detectable signal). In another embodiment, the functional reporter molecule can be detected without addition of exogenous substrate by measurement of some endogenous property (e.g., luminescence, chemiluminescence). Exemplary systems that permit detection of a signal without the addition of exogenous substrate include, but are not limited to FRET and BRET fluorescent transfer protein systems.

In embodiments where the functional reporter molecule is an enzyme that converts a substrate to a detectable product; the detection step typically first requires contacting the cell with a substrate for the reporter enzyme. The substrate may be contacted with the lysate using any convenient protocol. The nature of the particular substrate necessarily depends on the nature of the reporter enzyme which is present in the two fragments. For example, the substrate can be one that is converted by the reporter enzyme into a chromogenic product. Of interest in certain embodiments are substrates that are converted by the enzyme into a fluorescent product. The amount of substrate that is contacted with the lysate may vary, but typically ranges from about 1 femtomolar to 10 millimolar.

The substrate conversion can be evaluated in whole cells using methods known in the art. Exemplary methods include flow cytometric analysis, luminescent analysis, chemiluminescent analysis, histochemistry, fluorescent microscopy, and the like. The translocation events can be monitored in real time or following a predetermined incubation time after the initiating event. The cell is evaluated for the presence or absence of detectable signal (or product). The particular detection protocol employed varies depending on the nature of the detectable signal. For example, where the detectable product is a fluorescent product, the detection protocol employs the use of a fluorescent light detection means, e.g., a fluorescent light scanner, which can scan the lysate for the presence of fluorescent signal. The presence or absence of detectable signal from the signal producing system, e.g., detectable product in the cell, is then used to derive information as to whether translocation occurred. The presence or absence of a signal in the lysate is indicative of translocation, depending on the design of the reporter components. The signal can be correlated to the translocation event in a qualitative or quantitative manner. One also can employ a threshold value, whereby any signal above the threshold value represents insufficient activity and any signal below the threshold value represents sufficient activity. One also can evaluate the signal in a quantitative or a semi-quantitative manner, in which the amount of signal detected is used as a direct indication of the level of translocation events. The amount of signal detected may be linear or non-linear relative to the amount of translocation depending on the sensitivity of the reporter molecule and substrate employed. In one embodiment, a larger amount of signal indicates a greater amount of translocation, such that the amount of signal has a direct relationship with the amount of translocation.

The above signal evaluation may be accomplished using any convenient means. Thus, the signal may be subjectively evaluated by comparing the signal to a set of control signals. The evaluation may be done manually or using a computing or data processing means that compares the detected signal with a set of control values to automatically provide a value for the cell fusion activity. Quantified interactions can be expressed in terms of a concentration of signal molecule, translocation modulating compound (as described in the section below), or protein component required for emission of a signal that is 50% of the maximum signal ($IC_{50}$). Also, quantified interactions can be expressed as a dissociation constant ($K_d$ or $K_i$) using kinetic methods known in the art.

Translocation events have occurred when the signal produced by the functional reporter molecule in the system is different after exposure to an translocation initiating event or signal than the signal produced in a system in the absence of exposure to this event or signal. In one embodiment, a difference in signal is a reduction or elimination of signal produced by the functional reporter molecule following the initiating event or signal as compared to the signal produced by the functional reporter molecule in the absence of the event or signal. In other embodiments, a difference in signal is an increase in the signal produced by the functional reporter molecule following the initiating event or signal as compared to the signal produced by the functional reporter molecule in the absence of the event or signal.

Any suitable initiating event or signal may be employed in the methods provided herein. In one embodiment, translocation is inducible. Inducing signals include the initiation of one or more signaling cascades in response to hormones, cytokines, growth factors, pharmaceutical agents, external stressors, or some combination thereof. Cells can be exposed to one or more signals simultaneously or sequentially. Exemplary signals include but are not limited to PMA, irradiation, osmotic shock, heat, cold, hypoxia, tension, lipids, carbohydrates, metal ion withdrawal, calcium changes, growth factor/serum deprivation as well as those inducers discussed above.

In the methods provided herein, the signal generated by enzyme activity is often secondary to the translocation event and thus affects the study of processes in real time. Using high concentrations of dexamethasone, complete translocation of the glucocorticoid receptor occurs in 10-15 min, however the signal measured from β-galactosidase activity although detectable at 15 minutes, continued to increase over the next 180 min. By contrast the kinetics of the plasma membrane system was more predictable. Thus, the detection of the signal may be somewhat delayed relative to the translocation event itself.

Perhaps most importantly for applications that may utilize these methods, is the ability to accurately reflect levels of input and output in different systems. Using the glucocorticoid receptor in the nuclear translocation assay, enzyme complementation accurately described the ligand concentration at 10-fold intervals over a 1000-fold range. Even more sensitive was the C1A domain in the membrane translocation assay, detecting as little as 0.25 nM PMA (30% increase) and saturating at 800 nM PMA (1000% increase). In a more physiologically relevant setting, the enzyme complementation system correctly ordered the stimuli according to their ability to generate phospholipids, sorbitol>PDGF>insulin through monitoring the translocation of the AKT PH domain. See Examples below. Further, significant increases in phospholipid production were also apparent when the stimuli were added sequentially.

Thus, the methods provided herein permit the detection of translocation events that typically are not discernible by microscopy because signal generation is dependent on protein contact. Moreover, diffuse cellular structures or locations that are difficult to visualize using fluorescent proteins are made accessible for analysis by this technology.

In one aspect, provided herein is a method of sorting or for detecting at least one live cell where protein translocation is induced or modified in a cell mixture, comprising separating the cells of the methods provided herein according to the degree they are generate said signal from said first and second reporter components, using flow cytometric cell analysis.

In another aspect, provided herein is a method to visualize intracellular translocation in real time comprising detecting the signal generated in the cells of the methods provided herein using confocal microscopy.

Translocation Detection Methods Using β-Galactosidase

In a particular embodiment of the translocation detection assays providing herein, the reporter β-galactosidase is employed. The reporter components comprise two inactive fragments of β-galactosidase. The first reporter component is a short α peptide of β-galactosidase. In one embodiment, the α peptide comprises amino acids 5-51 of β-galactosidase. However, the a peptide can be smaller as long as it includes amino acid 46 of β-galactosidase. In some embodiments, the α peptide comprises the H31R mutation. Exemplary α peptides sequences include:

```
(wildtype)
                                         SEQ ID NO: 1
MGVITDSLAVVLQRRDWENPGVTQLNRLAAHPPFASWRNSEEARTDRPSQ
QL (H31R)
                                         SEQ ID NO: 2
MGVITDSLAVVLQRRDWENPGVTQLNRLAARPPFASWRNSEEARTDRPSQ
QL (F34Y)
                                         SEQ ID NO: 3
MGVITDSLAVVLQRRDWENPGVTQLNRLAAHPPYASWRNSEEARTDRPSQ
QL (E41Q)
                                         SEQ ID NO: 4
MGVITDSLAVVLQRRDWENPGVTQLNRLAAHPPFASWRNSQEARTDRPSQ
QL (N39D)
                                         SEQ ID NO: 5
MGVITDSLAVVLQRRDWENPGVTQLNRLAAHPPFASWRDSEEARTDRPSQ
QL (Truncated)
                                         SEQ ID NO: 6
MGVITDSLAVVLQRRDWENPGVTQLNRLAAHPPFASWRDSEEA
```

The second reporter component of β-galactosidase is the β-galactosidase protein comprising at least one mutation or deletion in the region of amino acids 1-56, sometimes 11-44. In a specific embodiment, the second reporter component is the M15 or M112 deletion mutant (ω) of lacZ(β-galactosidase) that is missing amino acids 11-41 or 23-31. See Langley et al., *Proc. Nat'l Acad. Sci. USA* 72:1254-57 (1975). One exemplary ω peptide sequence is set forth as SEQ ID NO:7

```
(MGVITDSLAVVARTDRPSQQLRSLNGEWRFAWFPAPEAVPESWLECDLP

EADTVVVPSNWQMHGYDAPIYTNVTYPITVNPPFVPTENPTGCYSLTFNV

DESWLQEGQTRIIFDGVNSAFHLWCNGRWVGYGQDSRLPSEFDLSAFLRA

GENRLAVMVLRWSDGSYLEDQDMWRMSGIFRDVSLLHKPITQISDFHVAT
```

-continued

```
RFNDDFSRAVLEAEVQMCGELRDYLRVTVSLWQGETQVASGTAPFGGEII

DERGGYADRVTLRLNVENPKLWSAEIPNLYRAVVELHTADGTLIEAEACD

VGFREVRIENGLLLLNGKPLLIRGVNRHEHHPLHGQVMDEQTMVQDILLM

KQNNFNAVRCSHYPNHPLWYTLCDRYGLYVVDEANIETHGMVPMNRLTDD

PRWLPAMSERVTRMVQRDRNHPSVIIWSLGNESGHGANHDALYRWIKSVD

PSRPVQYEGGGADTTATDIICPMYARVDEDQPFPAVPKWSIKKWLSLPGE

TRPLILCEYAHAMGNSLGGFAKYWQAFRQYPRLQGGFVWDWVDQSLIKYD

ENGNPWSAYGGDFGDTPNDRQFCMNGLVFADRTPHPALTEAKHQQQFFQF

RLSGQTIEVTSEYLFRHSDNELLHWMVALDGKPLASGEVPLDVAPQGKQL

IELPELPQPESAGQLWLTVRVVQPNATAWSEAGHISAWQQWRLAENLSVT

LPAASHAIPHLTTSEMDFCIELGNKRWQFNRQSGFLSQMWIGDKKQLLTP

LRDQFTRAPLDNDIGVSEATRIDPNAWVERWKAAGHYQAEAALLQCTADT

LADAVLITTAHAWQHQGKTLFISRKTYRIDGSGQMAITVDVEVASDTPHP

ARIGLNCQLAQVAERVNWLGLGPQENYPDRLTAACFDRWDLPLSDMYTPY

VFPSENGLRCGTRELNYGPHQWRGDFQFNISRYSQQQLMETSHRHLLHAE

EGTWLNIDGFHMGIGGDDSWSPSVSAEFQLSAGRYHYQLVWCQK).
```

In one example, the ω peptide is localized to a specific subcellular region using any suitable method. The ω peptide can be localized to a specific subcellular region using any suitable method. Exemplary methods include, but are not limited fusion to a targeting peptide, or a peptide sequence that is modified by a cellular process such as lipid modification, cleavage, or intein modification. The α peptide is fused to the protein of interest and expressed in the target cell. The ω and α peptides are typically expressed in silu using an expression system. Typically, each will be expressed in a separate specific subcellular region. Specific subcellular regions include, but are not limited to nucleus, cytoplasm, membrane, endosome, mitochondria, golgi, nuclear membrane, nucleolus, ER, actin or microtubule cytoskeleton, lysosome, PML bodies, chromatin, P bodies, plasma membrane (exterior and interior), axon, dendrite, filopodia, and the like. When the fusion protein moves into proximity of the ω peptide, the ensuing complementation results in enzyme activity that can be monitored in live cells by any suitable method including, but not limited to flow cytometry and a highly sensitive luminescent assay. See, e.g., Nolan et al., *Proc. Natl. Acad. Sci. USA* 85:2603-07 (1988); Martin et al., *Biotechniques* 21:520-24 (1996). Because the signal is amplified enzymatically, the translocation events can be detected at physiologically relevant expression levels of target protein. This permits 10-100 fold increase in sensitivity and a 10-fold signal-to-noise ratio. Further, the enhanced signal generated using this method combined with the low sample variability synergize to create a highly sensitive and quantitative measure of protein localization.

Also provided herein are the nucleic acid sequences as set forth in SEQ ID NO:1, SEQ ID NO:2. SEQ ID NO:3, SEQ ID NO:4, SEQ ID NO:5, SEQ ID NO:5, SEQ ID NO:6, SEQ ID NO:7, SEQ ID NO:8, and SEQ ID NO:9, the polypeptides encoded by these sequences, vectors expressing sequences, as well as cell comprising the vector or the nucleic acid.

In a specific embodiment, the α peptide employed is one that complements the ω peptide robustly in mammalian cells. The high affinity minimal α peptide permits sensitive, accurate analysis of protein translocation events between compartments physically separated by a membrane with only a minimum of translocation events required for detection. Exemplary high affinity peptides include SEQ ID NO: 8
MGVITDSLAVVLQRRDWENPGVTQLNR-LAAHPPFASWRNSEEARTDRPSQ QL; and

SEQ ID NO: 9 (W37Y)
MGVITDSLAVVLQRRDWENPGVTQLNR-LAAHPPFASYRNSEEARTDRPSQQL.

) Such high affinity a peptides are not suitable for translocation events that take place in the same compartment such as those from the cytosol to the plasma membrane.

For example, in the embodiment where the chimeric fused protein produced intracellularly includes the alpha peptide and a protein of interest, β-gal activity results when the fused protein moves to the same compartment as the ω peptide and will be proportional to the amount of protein that is translocated to that compartment. Thus, the β-gal activity is driven by the translocation of the protein of interest, not by the complementing β-gal peptides themselves. The enzymatic activity serves as readily detectable indicator of that interaction. Another advantage of this system is that only low levels of expression of the test proteins are required to detect translocation.

Any suitable method for detecting β-gal activity may be employed. Such method include, but are not limited to live-cell flow cytometry and histochemical staining with the chromogenic substrate 5-bromo-4-chloro-3-indolyl β-D-galactopyranoside (X-Gal). See, e.g., Nolan et al., *Proc. Natl. Acad. Sci. USA* 85:2603-07 (1988); LOJDA, Z., ENZYME HISTOCHEMISTRY: A LABORATORY MANUAL (Springer, Berlin 1979). Histochemical staining for β-gal can be achieved by fixation of cells followed by exposure to X-gal.

In one embodiment, intracellular analyses may be conducted by fixing cells and staining with the indigogenic substrate X-gal. See, e.g., Mohler and Blau, *Proc. Natl. Acad. Sci. U.S.A.* 93:12423-27 (1996); U.S. Pat. No. 6,342,345. Fixed cells also can be analyzed by assaying for β-gal activity by fluorescence histochemistry using an azo dye in combination with either X-gal or 5-bromo-6-chloro-3-indolyl β-D-galactopyranoside (5-6-X-Gal). A preferred combination is the azo dye red violet LB (Sigma Chemical, St. Louis, Mo.) and 5-6-X-Gal, referred to as Fluor-X-gal. For this combination, fluorescence micrographs can be obtained on a fluorescence microscope using a rhodamine/Texas Red filter set. Use of these substrates allows β-gal-dependent fluorescence to be visualized simultaneously with two or more other fluorescent signals.

Vital substrates for β-gal, which can be used in living cells, are also encompassed by the invention. For example, a vital fluorogenic substrate, resorufin β-galactoside bis-aminopropyl polyethylene glycol 1900 (RGPEG) has been described. See, e.g., Minden, *Bio Techniques* 20:122-29 (1996). This compound can be delivered to cells by microinjection, electroporation or a variety of bulk-loading techniques. Once inside a cell, the substrate is unable to escape through the plasma membrane or by gap junctions. Another vital substrate that can be used in the practice of the invention is fluorescein di-β-D-galactopyranoside (FDG), which is especially well-suited for analysis by fluorescence-activated cell sorting (FACS) and flow cytometry. See, e.g., Nolan et al. *Proc. Natl. Acad. Sci. USA* 85:2603-07 (1988); Rotman et al., *Proc. Natl. Acad. Sci. USA* 50:1-6 (1963).

β-gal may also be detected using a chemiluminescence assay. For example, cells containing β-gal fusions are lysed in a mixture of buffers containing Galacton Plus substrate from a Galactolight Plus assay kit (Tropix, Bedford Mass.). See, e.g., Bronstein et al, *J. Biolumin. Chemilumin.*, 4:99-111 (1989). After addition of Light Emission Accelerator solution, luminescence is measured in a luminometer or a scintillation counter.

Representative substrates that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbel-liferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galacto-pyranoside, 5-bromo-4-chloro-3-indolyl-β-D-galactopynanoside, resorufin-β-D-galactopyranoside, 7-hydroxy-4-trifluoromethyl coumarin, Ω-nitrostyryl-β-D-galactopyranoside, and flourescein-β-D-galactopyranoside. See, e.g., U.S. Pat. No. 5,444,161.

Identification of Modulators of Protein Translocation

The methods provided herein can also be employed to identify modulators of protein translocation in situ. A method for identifying a modulator of protein translocation, comprising: (a) providing a first reporter component to a cell, wherein said first reporter component is coupled to a protein of interest; (b) providing a second reporter component capable of forming an active complex with said first reporter component to generate a detectable signal, to said cell, wherein said second reporter component is localized to a specific subcellular region; (c) providing a signal to said cell that induces the translocation of one of said reporter components, wherein the translocation results in the formation of said active complex via the binding of said first reporter component to said second reporter component when both components are localized to said specific subcellular region; (d) contacting said cell with a candidate modulator compound; and (e) detecting a signal produced by said active complex in the presence of said candidate compound relative to that signal produced by said active complex in the absence of said candidate modulator compound, whereby said candidate compound is identified as said modulator compound whose presence results in a measurably different signal from the signal generated in the absence of said candidate modulator compound.

Using the methods provided above, a candidate compound is identified as a modulator of in situ protein translocation event when the signal produced by the functional reporter molecule in the system contacted with the candidate compound is different than the signal produced in a system not contacted by the candidate compound. A difference in signal can be a reduction or elimination of signal produced by the functional reporter molecule in the presence of the candidate compound as compared to the signal produced by the functional reporter molecule in the absence of the candidate compound. In other embodiments, a difference in signal can be an increase in signal produced by the functional reporter molecule in the presence of the candidate compound as compared to the signal produced by the functional reporter molecule in the absence of the candidate compound.

A variety of different modulator molecules may be identified using the method as provided herein. Candidate compounds can encompass numerous chemical classes. In certain embodiments, they are organic molecules, preferably small organic compounds having a molecular weight of more than 50 and less than about 2,500 daltons. Candidate compounds can comprise functional groups necessary for structural interaction with proteins, particularly hydrogen bonding, and may include at least an amine, carbonyl, hydroxyl or carboxyl group, preferably at least two of the functional chemical groups. Candidate compounds can comprise cyclical carbon or heterocyclic structures and/or aromatic or polyaromatic structures substituted with one or more of the above functional groups. Candidate compounds are also include biomolecules like peptides, saccharides, fatty acids, steroids, purines, pyrimidines, derivatives, structural analogs or combinations thereof. Candidate compounds also can include peptide and protein agents, such as antibodies or binding fragments or mimetics thereof, e.g., Fv, $F(ab')_2$ and Fab.

Candidate compounds also can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In one embodiment, a candidate compound is identified as a modulator of protein translocation when it is capable of specifically modulating the translocation of a protein of interest by reducing the rate or amount of translocation mediated by the translocation initiating event(s) at least about 5, 10, 15, 20, 25, 30, 35, 40, 45 or 50%, often 60, 70, 80 or 90%, and sometimes 100%. In other embodiments, a candidate compound is identified as a modulator of protein translocation when it is capable of specifically modulating the translocation of a protein of interest by increasing the rate or amount of translocation mediated by the translocation initiating event(s) at least about 5, 10, 15, 20, 25, 30, 35, 40, 45 or 50%, often 60, 70, 80, 90%, or 100%, and sometime about 200, 500, 1000% or greater. As used herein, the term "rate or amount of protein translocation" refers to the total quantity of protein translocation per unit time. A modulator of protein translocation is one whose activity results in a change in the cellular response to the translocation initiating event. Such cellular responses include inhibition of apoptosis, inhibition of cell growth, induction of apoptosis, induction or cell growth, and the like.

The amount of candidate compound that is present in the contact mixture may vary, particularly depending on the nature of the compound. In one embodiment, where the agent is a small organic molecule, the amount of cell fusion inhibitory molecule present in the reaction mixture can range from about 1 femtomolar to 10 millimolar. In another embodiment, where the agent is an antibody or binding fragment thereof, the amount of the cell fusion inhibitory molecule can range from about 1 femtomolar to 10 millimolar. The amount of any particular agent to include in a given contact volume can be readily determined empirically using methods known to those of skill in the art.

As described above, the presence or absence of detectable signal is determined from the translocation of the reporter components into the same subcellular compartment. The signal can be correlated to the modulatory activity of the candidate and therefore is used to determine the modulatory activity of a candidate compound using the increase or decrease of signal as appropriate to the method design. Protein translocation modulation can be expressed as % translocation, rate of translocation, $IC_{50}$, $K_d$, or other suitable measurement relative to baseline controls.

The above signal evaluation as a determination of the modulatory activity may be accomplished using any convenient means. Thus, the signal may be subjectively evaluated by comparing the signal to a set of control signals. The evaluation may be done manually or using a computing or data processing means.

The above protein translocation protocols are amenable to high throughput formats, by which is meant that the above translocation assays can be performed in an automated fashion to screen a plurality of different test cell fusion inhibitor molecules simultaneously. As such, large numbers of compounds can be screened using automated means at substantially the same time. In one embodiment, at least about 10,000 to 1,000,000 compounds can be screened simultaneously. In these high throughput formats, one or more of the above steps, including all of the steps, may be automated, including candidate compound contact, signal detection and signal evaluation. Such high-throughput assays will be especially valuable in screening for drugs that influence medically-relevant protein translocation events.

No-Wash ELISA Method

Provided herein is a method for a no-wash ELISA. Several of the advantages of the present invention include (1) a single plate can be used to detect more than one analyte, (2) less sample volume is used in the assay, (3) less reagent volume is used in the assay, (3) the assay can be adapted to automated protocols, (4) a single plate can be used to detect diseases which have more than one determinant or marker, (5) a single plate can be used to detect recombinant organisms, including transgenic organisms, which express more than one determinant or marker, and (6) a single plate can be used to detect more than one pathogen in a sample; (7) there are fewer steps and thus fewer possible technician errors; and (8) decreased process time and equipment required for analysis.

Thus, provided herein is a method for a no-wash ELISA assay for detecting a compound in a sample, comprising: (a) immobilizing a first reporter component and a first agent that binds said compound on a support; (b) contacting said support with a solution comprising said compound; (c) adding a second receptor component coupled to a second agent that binds said compound; (d) forming an active complex of said first and second reporter components, wherein said complex is mediated by binding of said second agent to said compound bound to said first agent; and (e) detecting a signal that is measurably different from a signal generated when said compound is not bound. The various steps of the assay may be performed sequentially or by combining various steps. For example, steps (b) and (c) may be performed separately or simultaneously.

In a particular embodiment of the no-wash ELISA assays providing herein, the reporter β-galactosidase is employed. The reporter components comprise two inactive fragments of β-galactosidase. One reporter component is the M15 deletion mutant (ω peptide) of lacZ(β-galactosidase) that is missing amino acids 11-44. The first reporter can also be the M112 mutant ω peptide. See Langley et al., Proc. Nat'l Acad. Sci. USA 72:1254-57 (1975). The complementing reporter component is a short α peptide of β-galactosidase. The α peptide can comprise amino acids 5-51 of β-galactosidase. In some embodiments, the α peptide comprises the H31R mutation. Exemplary α peptides sequences include SEQ ID NO: 1, 2, 3, 4, 5, and 6 as disclosed herein. The complementing reporter component of β-galactosidase is the β-galactosidase protein comprising at least one mutation or deletion in the region of amino acids 11-44 or 23-31. One specific ω peptide is as set forth in SEQ ID NO:7. Either component may be immobilized initially on the solid support.

Any suitable agent can be used that bind the compound of interest. In one embodiment, the agent is an antibody. Any suitable antibody or biologically relevant fragment thereof may be employed in the methods provided herein. The antibody of the present methods and compositions can be monoclonal or polyclonal. The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be. used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clarkson et al., Nature 352: 624-628 (1991) and Marks et al., J. Mol. Biol. 222: 581-597 (1991), for example.

The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, the antibody useful in the present methods is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition).

Any form of the antigen can be used to generate the antibody that is sufficient to generate a specific antibody for the target antigen. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell.

Any suitable compound can be detected using these methods. In some embodiments, the compound is an antigen. In one embodiment, the antigen is a pollutant. Exemplary pollutants include, but are not limited to PCB, flucythrinate, and organochlorine compounds. In a specific embodiment, the pollutant is vitellogenin.

In some embodiment, the no-was ELISA method may be used to detect the present of antibodies in a sample, typically a biological sample such as blood, serum, urine, and the like.

If a second antibody is required for antigen detection, any suitable method can be used to label the antibody. Frequently, the antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., *Nat. Biotechnol.* 21:1473-79 (2003).

The reporter component and agents can be immobilized on the support any suitable means. Exemplary methods include, but are not limited to adsorption, entrapment, and covalent linkages to the support. See, e.g., CASS ET AL., EDS. IMMOBILIZED BIOMOLECULES IN ANALYSIS: A PRACTICAL APPROACH (Oxford University Press 1998). As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, and alumina gels. In one embodiment, the solid support is a 96 well plate, an ELISA plate, bead, particle, glass, silica, plastic, nylon or nitrocellulose.

Suitable substrates and detection methods are described above. Any suitable means of performing colorimetric, fluorometric, or other analysis can be used. The sample may be prepared by any convenient means.

Kits

Kits employing the methods described above also are provided herein. Thus, provided herein is a kit for assessing the local concentration of a compound comprising: (a) a nucleic acid sequence as set forth in SEQ ID NO: 1, SEQ ID NO:2, SEQ ID NO:3, SEQ ID NO:4, SEQ ID NO:5, SEQ ID NO:6, SEQ ID NO:8, or SEQ ID NO:9. or vector comprising said sequence; (b) a nucleic acid sequence as set for in SEQ ID NO:7 or vector comprising said sequence; and (c) optionally, instructions for use of said nucleic acid sequences. The compositions provided in the kit may further contain any surfactant, preservative, stabilizer, and enzyme activator. In some embodiments, standards for calibration of the assay are included.

EXAMPLES

Example 1

Design of the Minimal Fragment

α-complementation of β-galactosidase involves a deletion mutant, the ω fragment (ω), that is missing amino acids 11-41. In *E. coli* and in vitro, it is possible to complement this mutant in trans by providing the α peptide which encodes amino acids 3-41. However, previous studies in mammalian cells reported that the smallest complementing fragment contained amino acids 1-71. Because a smaller peptide enhances the efficiency of anal sensitivity, the smallest α peptide(s) that would complement robustly in mammalian cells when fused to an exogenous protein at the N or C tenninus was determined. The myoblast cell line C2C12 was engineered to stably express the ω fragment by retroviral transduction. The α portion of β-galactosidase was fused to the C-terminus of GFP and deletions were made starting at amino acids 137 and continuing through amino acids 38. The products were transduced into the parental cell line expressing the ω-fragment, and the cells were sorted by FACS for similar GFP expression levels.

In FIG. 1A, the right panel shows the first 137 amino acids of β-galactosidase fused to the C-terminus of GFP and serially truncated. These constructs were co-expressed with the ω in mouse myoblast C2C 12 cells and assayed for β-galactosidase activity using the luminescent assay. Cells were plated in 96-well dishes and assayed for β-galactosidase activity using a 1,2 dioxetane luminescent substrate. In FIG. 1A, the left panel shows amino acids 1-51 of β-galactosidase fused to the N-terminus of GFP, serially truncated, then co-expressed with the ω fragment. The minimal fragment was defined by combining the last C-terminal (47R) and N-terminal (5D) truncations which were then fused to the N and C terminus of GFP. These fusions were co-expressed with the ω fragment and assayed for enzyme activity.

Truncations past amino acids 49 result in a 10-fold decrease in β-galactosidase activity. To determine which residues could be deleted at the N-terminus, amino acids 1-51 were fused to the N-terminus of GFP and deletions were made starting at amino acids 5. These constructs were similarly transduced into the parental C2C12 cell line expressing the ω-fragment. Deletions past amino acids 5 resulted in a 100-fold decrease in β-galactosidase activity (FIG. 1A left panel), combining these deletions the minimal complementing fragment in mammalian cells should encompass amino acids 5-49. To ensure this peptide would complement at the same level when fused to either the amino or carboxy terminus of a protein, the peptide was fused separately to either end of GFP (FIG. 1C). When the peptide was expressed as a C-terminal fusion, robust complementation was achieved; however, fusion of the same peptide to the N-terminus resulted in 100 fold less activity. Thus, in order to maintain consistency for the ensuing studies amino acids 5-51 (designated α) is the minimal fragment that complements to high activity in mammalian cells when expressed as a fusion protein in any orientation.

Example 2

Nuclear Translocation Assay

Figure 2:
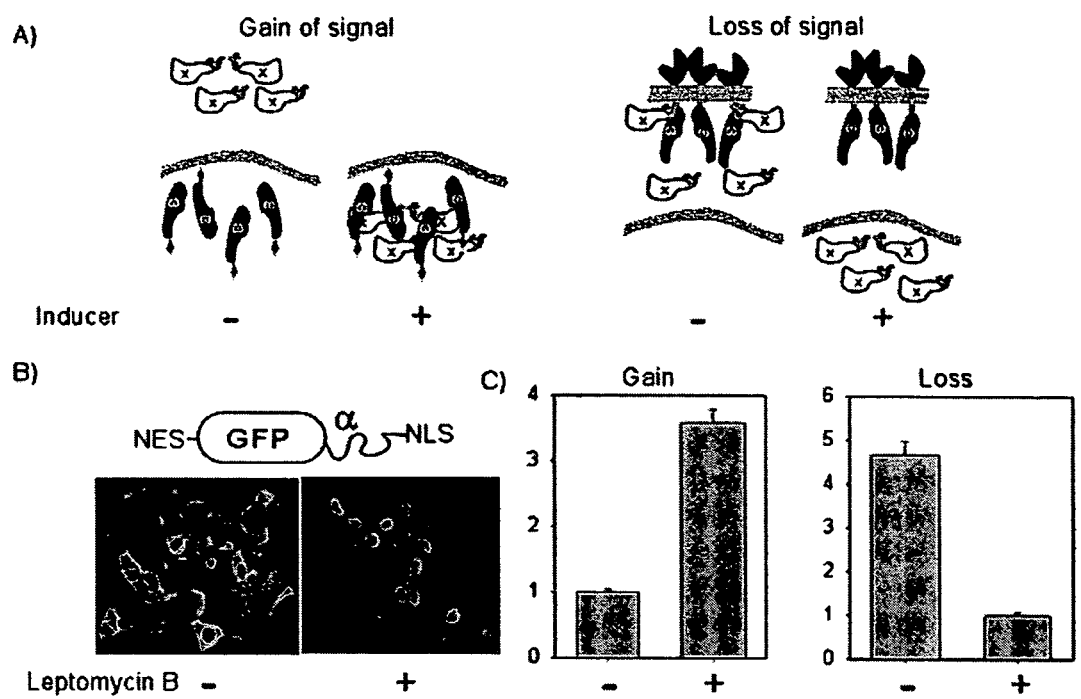
FIG. 2 depicts enzyme complementation used to assay nuclear translocation.

In order to utilize α complementation as a method of quantitatively assessing nuclear translocation events, two systems were designed that are distinct in the localization of the ω-fragment. FIG. 2A is a schematic showing the design of the nuclear translocation assay. In the left panel, the ω fragment is localized to the nucleus with a nuclear localization signal (NLS) and the cytosolic protein of interest is fused to the minimal α peptide. Upon stimulation the α fusion moves to the nucleus and complements the ω, increasing β-galactosidase activity. In the right panel, the ω fragment is tethered to the plasma membrane using the extracellular and transmembrane regions of EGFR. The cytosolic α-fusion complements spontaneously until stimulation when it translocates to the nucleus which results in a loss of enzyme activity.

The gain of signal assay (FIG. 2A left panel) localized the ω to the nucleus through fusion to a triplet SV40 nuclear localization signal (NLS). Thus, an increase in β-galactosidase activity should be observed when the target protein-α fusion moves from the cytosol to the nucleus. The loss of signal assay (FIG. 2A right panel) localized the ω-fragment to the plasma membrane through fusion to the extracellular and transmembrane regions of the EGF receptor (tEGFR). This configuration resulted in a decrease in β-galactosidase activity when the target protein-α translocated to the nucleus (FIG. 2A).

As a test system for nuclear translocation, a GFP-α fusion was created that contains the nuclear export signal from MEK and a triplet SV40 NLS. See FIG. 2B. Left Panel shows a fusion protein consisting of the mitogen activated protein kinase kinase (MAPKK or MEK) segment that acted as a nuclear export signal fused to GFP, the α peptide and a triplet SV40 NLS. See NES; Fisher et al., Cell, 82:475-83 (1995); Wen et al., Cell, 82:463-73 (1995). At steady state the protein was cytosolic. In the presence of leptomycin B, the protein became nuclear.

Thus, at steady-state, the protein was almost exclusively located in the cytosol, but in the presence of leptomycin B, which blocked Crml mediated nuclear export, the protein was retained in the nucleus. The GFP-α fusion was transduced separately into C2C12 myoblasts expressing either the ω-NLS or the tEGFR-ω construct. In the gain of signal assay, addition of leptomycin B for 2 hours resulted in a 3.5 fold increase in β-galactosidase activity assayed using the luminescent substrate. Similarly, addition of leptomycin B to the loss of signal assay resulted in almost a five-fold decrease in β-galactosidase activity (FIG. 2B, right panel). These results demonstrated that complementation systems can be used to monitor protein translocation events in mammalian cells.

FIG. 2C shows a gain of signal assay. In the left panel, the NES-GFP-α-NLS protein was coexpressed with the ω-NLS. Addition of leptomycin B for 2.5 hours resulted in a gain of β-galactosidase activity. A loss of signal assay is shown in the right panel. Transduction of cells expressing the tEGFR-w fusion with the NES-GFP-α-NLS construct resulted in a loss of β-galactosidase activity in the presence of leptomycin B.

To test the applicability of the system to a physiological translocation event the glucocorticoid receptor was fused to the amino-terminus of the GFP-α fusion. The glucocorticoid receptor is a nuclear steroid hormone receptor that undergoes a robust nuclear translocation in response to treatment with various hormones including dexamethasone. This construct was stably introduced into both the ω-NLS and tEGFR-ω cell lines then assayed for changes in β-galactosidase activity upon treatment of the cells with dexamethasone using the luminescent β-galactosidase substrate.

Figure 3:
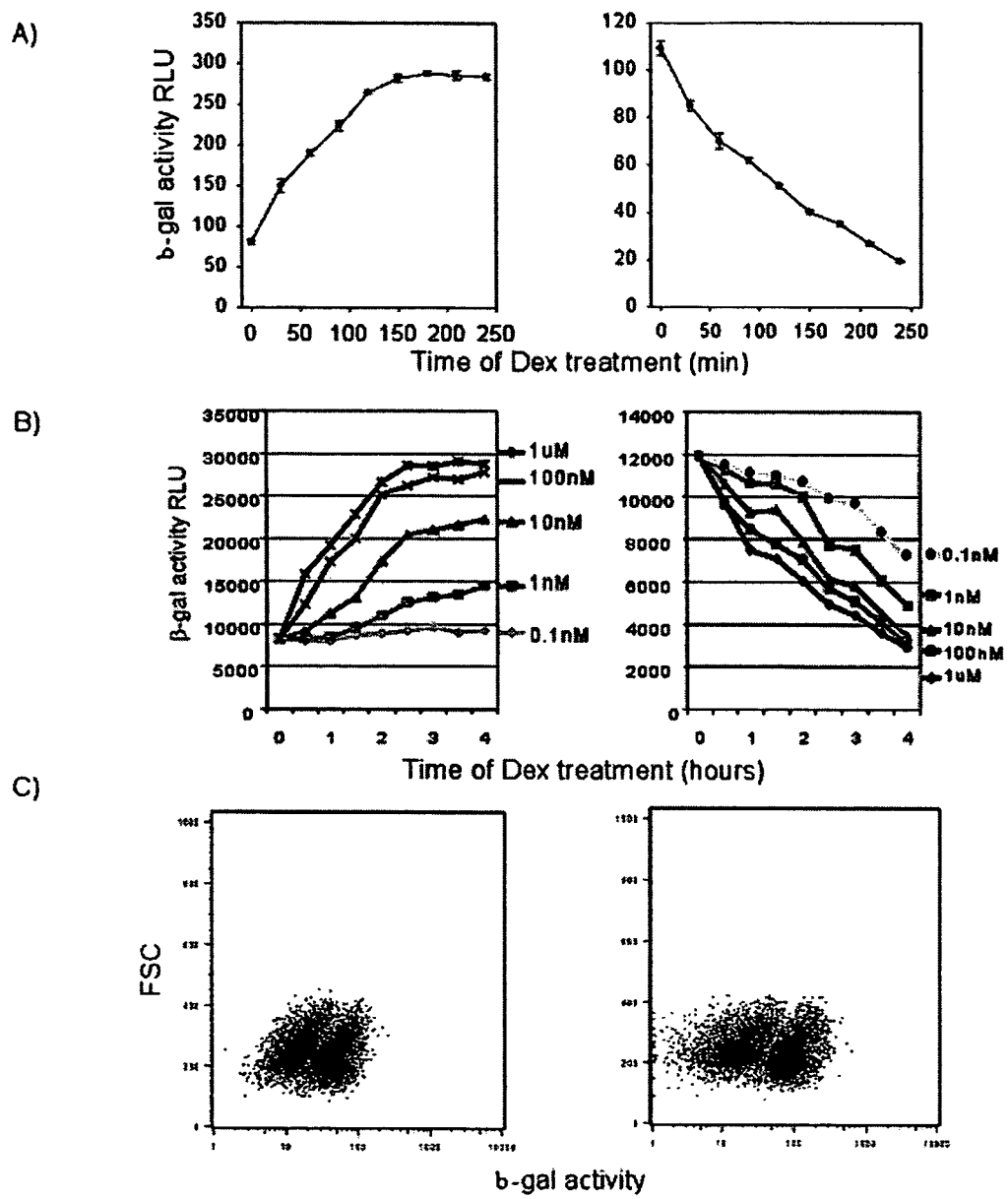
FIG. 3 shows a nuclear translocation of the glucocorticoid receptor monitored by enzyme complementation.

FIG. 3A shows a time course of cells expressing the GR-α fusion and either the ω-NLS (Left) or tEGFR-ω (right) and assayed for β-galactosidase activity after treatment with 1 μM dexamethasone for the indicated times. FIG. 3B shows dose versus time. Cell lines shown in FIG. 3A were treated with varying concentrations of dexamethasone and assayed over time. FIG. 3C shows protein localization monitored by flow cytometry. The GR-α cell lines were treated with 1 μM dexamethasone (red) for 3 hours then stained with the fluorescent β-galactosidase DDAO substrate and analyzed by flow cytometry.

Addition of 1 μM dexamethasone for 3 hours to the gain of signal assay resulted in a 3.5 fold induction of β-galactosidase activity, while the loss of signal assay showed a slightly better signal to noise ratio of approximately 5-fold (FIG. 3A). The ability to maintain complementation efficiency when fused to the large fusion protein (GR-GFP) suggests that complementation can take place with proteins at least 120 KD in size.

Although differences in β-galactosidase activity were discernible as early as 30 min of treatment (100% for the gain of signal assay, and 25% for the loss of signal assay) visualization of the translocation event by GFP fluorescence shows that most of the protein has translocated by this time, however the differences in β-galactosidase activity continue to accumulate over the next three hours. α complementation in vitro using purified proteins required 30-60 min to reach equilibrium. The lag in β-galactosidase activity may be due at least in part to the time of competent enzyme formation (gain) and breakdown (loss). Importantly, the dose response assayed over time demonstrated the ability of the system to discern different levels of stimulus (FIG. 3B). Consistently over a period of four hours, the gain of signal assay was able to significantly detect 10-fold differences in dexamethasone concentration over a $10^3$ fold range. The loss of signal assay showed a higher sensitivity to low concentrations of dexamethasone, yet maintained the ability to differentiate between concentrations ranging from 0.1 to 10 nM.

Assaying protein movement through enzyme complementation permitted the use of a wide variety of substrates and detection methods, including several fluorescent β-galactosidase substrates. The GR-GFP-α cell lines were assayed in the presence and absence of dexamethasone for 3 hours using the fluorescent β-galactosidase substrate DDAO (FIG. 3C). Both systems showed a 5-10 fold change in β-galactosidase activity in the presence of dexamethasone when assayed in live cells by flow cytometry. Significantly, this was the first report of flow cytometry being used to distinguish cells based solely on the location of an intracellular protein.

Example 3

α-peptide Mutants with Diminished Complementation Capacity

The α peptide used in the nuclear translocation assay had the capability of spontaneously restoring enzyme activity when placed in the same cellular compartment as the ω mutant. Although this method is ideal for proteins that can be separated from the ω by a physical barrier, a system to identify translocation events within the same cellular compartment also benefited from α peptides that bind the ω with lower affinity. β-galactosidase is active only as a tetramer. The crystal structure of β-galactosidase shows that residues 5-28 of the α peptide are involved in dimerization of two monomers while residues 31-41 are buried within the ω fragment. Without being bound by theory, mutation of the buried residues could decrease the ability of the α peptide to dock with the ω fragment while maintaining its ability to mediate tetramer formation.

Figure 4:
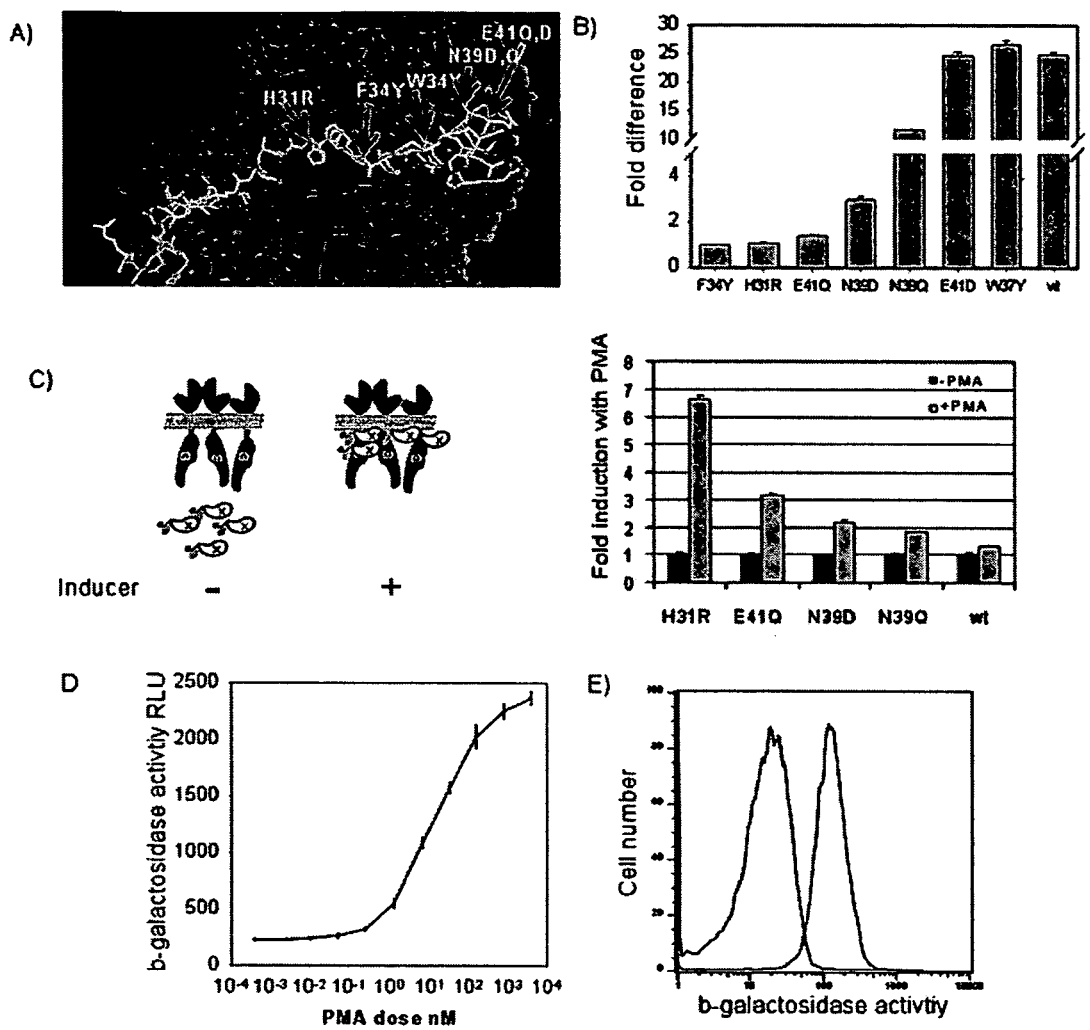
FIG. 4 shows mutation of the α-peptide to generate weakly complementing mutants.

Several point mutations spanning residues 31-41 were engineered into the α fused to the carboxy terminus of GFP (FIG. 4). FIG. 4A shows the crystal structure of wild type β-galactosidase with the α peptide pictured in yellow (light colored) and the mutations indicated. FIG. 4B shows mutations made in the α-peptide fused to the C-terminus of GFP. These constructs were transduced into the tEGFR-ω cell line, sorted for similar amounts of GFP expression, then assayed for β-galactosidase activity using the luminescent assay. Of the seven mutations, five decreased complemented enzyme activity from 2-25 fold (FIG. 4B).

Example 4

Plasma Membrane Translocation System

Creation of a plasma membrane translocation assay required expression of the ω fragment at the membrane which was achieved using the tEGFR-ω construct. When the target protein-α fusion move from the cytosol to the membrane, the local increased concentration of α peptide should drive complementation as illustrated in FIG. 4B. To determine which of the mutants would work best in this type of assay the C1A domain from PKCγ was fused to four of the GFP-α point mutants that complemented to varying degrees, H31R, E41Q, N39D, and N39Q. FIG. 4C shows a schematic of the membrane translocation assay. The ω fragment was tethered to the plasma membrane using the extracellular and transmembrane regions of the EGFR. Four of the mutants were fused to the C1A domain of PKCγ and coexpressed with the tEGFR. Their responses to 1 μM PMA for 20 min were expressed as a fold induction over background. The C1A domain efficiently translocated to the plasma membrane when exposed to phorbol esters such as PMA (FIG. 4C). The fusion proteins were expressed in NIH 3T3 cells expressing the tEGFR-ω, and assayed for increased complementation in the presence of PMA for 30 min. The fold induction of the various mutants was inversely proportional to the background activity for all of the mutants tested as well as the wt peptide which showed less than a 10% increase in β-galactosidase activity (FIG. 4A). The H31R mutant, which had the lowest background activity of the mutants tested, showed a remarkable 7-fold induction of β-galactosidase activity in the presence of PMA.

The translocation of the C1A domain in response to PMA stimulation has been extensively characterized by fusion to GFP. The largest increase in fluorescence at the plasma membrane in response to PMA was reported to be 70% with the lowest dose of PMA detected using these methods being between 10 and 100 nM. Using β-galactosidase complementation, 700-1000% increases in enzyme activity were achieved in the presence of PMA, and as little as 1 nM PMA could be detected in the medium (FIG. 4D). FIG. 4D shows a H31R dose response. The H31R mutant that showed the highest fold induction was treated with varying levels of PMA for 30 min and then assayed for β-galactosidase activity. Like the nuclear translocation assay, single cell analysis by flow cytometry in live cells using the DDAO fluorescent substrate showed a large increase in fluorescence upon induction of translocation (FIG. 4E). Importantly, the requirement of the ω fragment for complementation ensured that enzyme activity was only generated where the ω-fragment was localized. Thus, the assay measured increases in protein concentration at a specific location in the cell.

To test whether the system was robust enough to monitor translocation events in response to physiologically relevant stimuli, this system was applied to the translocation of the PH domain of AKT. The AKT PH domain binds PI 3,4,5 trisphosphate as well as PI 3,4 bisphosphate which are generated at the plasma membrane in response to various stimuli including peptide growth factors and cellular stresses. The PH domain of AKT was fused to the GFP-α chimera and expressed in 3T3 fibroblasts harboring the tEGFR-ω protein. FIG. 5A shows the AKT-GFP-α fusion protein transduced into 3T3 cells expressing the tEGFR-ω fusion. The cells were stimulated under various conditions, and the translocation of the PH domain was assayed in 96-well dishes by a luminescent measure of β-galactosidase activity. The cells were treated with 50 ng/ml PDGF, insulin, or sorbitol for the indicated times and assayed for β-galactosidase activity using the luminescent substrate. Osmotic shock showed the slowest, but largest increase in β-galactosidase activity (8-fold), followed by PDGF (5-fold), and insulin (2.5 fold) which agreed with biochemical quantifications using radioactive labeling and quantification of phospholipids. However, an advantage of using the PH domain as a sensor in the β-galactosidase was that only increases at the plasma membrane generate increased in β-galactosidase activity due to the localization of the ω. Further, the ability to perform these assays in high-throughput format made it possible to also perform detailed time course and dose response experiments.

The high signal to noise ratio and low standard deviations of the enzyme complementation system combined to generate a highly sensitive and quantitative assay for physiological events. This was most evident when the stimuli are applied sequentially. FIG. 5B shows a time course of stimulation with each of the four stimuli. After each stimulation the β-galactosidase compleinentation system registered sequential increases in activity. The cells used in FIG. 5A were sequentially stimulated with insulin, PDGF and Sorbitol and assayed for β-galactosidase activity. Insulin was applied first, then PDGF, sorbitol. The shapes of each curve were dependent on the stimulation used, indicating that the rates of phospholipid generation reflected the magnitude and rate of change in β-galactosidase activity.

Figure 6:
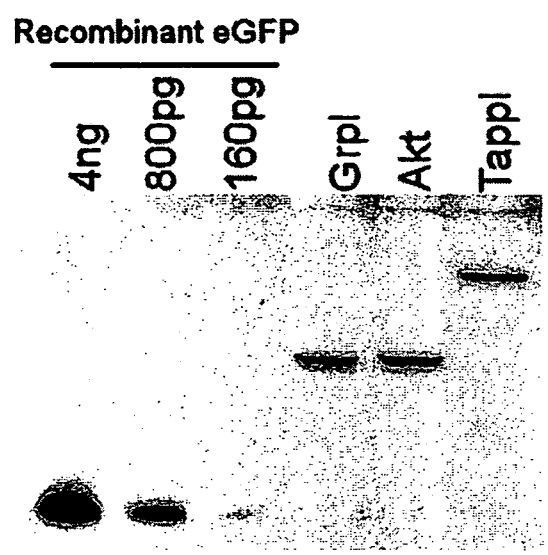
FIG. 6 shows total cell lysates from the cell lines expressing the indicated PH domains fused to the GFP-α chimera used in FIG. 5 immunoblotted for expression of the fusion protein. A titration of recombinant GFP was included to quantitate the levels of protein.

The plasma membrane translocation events may be imaged by using the fluorescence of the GFP molecule fused to the α fragment. However, toxicity associated with stable expression of these domains was a concern for expressing sufficient protein to image by conventional confocal microscopy. The amount of fusion protein expressed was quantified by immunoblotting the cell lines used in the β-galactosidase assays with a GFP antibody. The signal was compared to known amounts of purified GFP (FIG. 6). The amount of fusion protein expressed per μg was calculated to be approximately 50 pg/μg of protein for GrpI and 80 pg/μg for the AKT PH domain or 1 in 12-20,000th of total protein. The C1A domain was undetectable by Western blot. Assuming a 4 pL volume for 3T3 cells the expression level of these domains that were readily assayed by β-galactosidase activity, was 2-16 nM.

Example 5

Application of the Enzyme Complementation System to No-wash ELISA Protocols

The enzyme complementation system to monitor protein localization was applicable to a ELISA detection system. (See generally, ELISA and Other Solid Phase Immunoassays: Theoretical and Practical Aspects, Kemeny et aL, eds. Wiley, John & Sons, Incorporated (1996); Weir's Handbook of Experimental Immunology, Herzenberg, et al., eds. Blackwell Publishers (1996)). One of the translocations shown to be effectively monitored using this technique was movement from the cytosol to the interior of the plasma membrane. In the method provided, the large M15 β-galactosidase mutant was constitutively localized to the interior of a cell membrane. Translocation of a cytosolic protein conjugated to a low affinity peptide, either by truncation or mutation, resulted in measurable increases in β-galactosidase activity. A significant benefit of using the low affinity components was the elimination washing steps from the ELISA assay.

Figure 7:
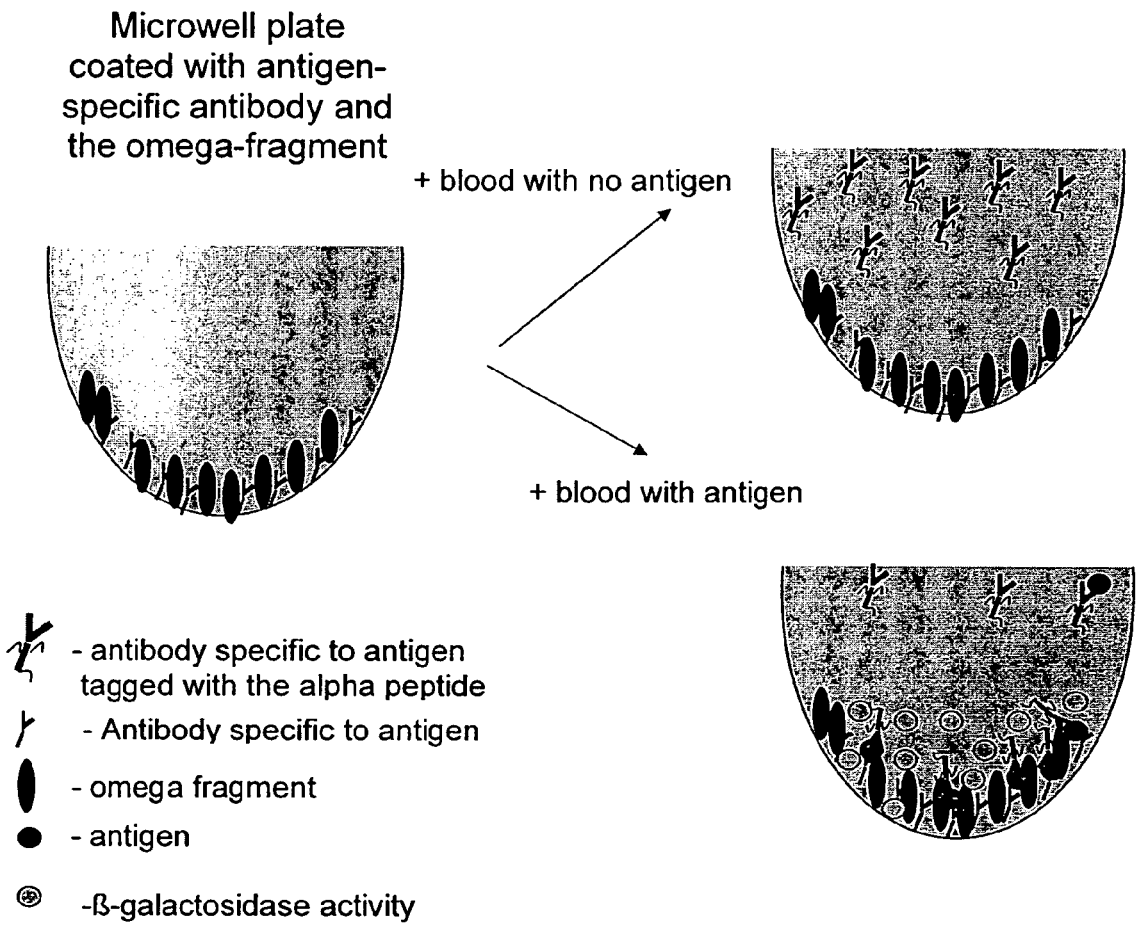
FIG. 7 shows a schematic of an ELISA assay according to the invention.

Using the same concept in in vitro systems using purified proteins enables a novel form of ELISA detection. An example of this technology using a standard Sandwich ELISA is depicted schematically in FIG. 7. The purified M15 β-galactosidase mutant low-affinity fragment was coated onto a substrate along with a primary antibody specific for a particular antigen. Alternately, the low-affinity fragment was conjugated to the antibody and coated on the substrate. The sample containing the antigen was then added to the plate and consequent binding of the antigen to the primary antibody occured. A secondary antibody (specific for a different epitope on the same antigen) conjugated to the complementary low affinity fragment (alpha peptide) was then also added. This binding brought the secondary antibody and hence the low affinity alpha peptide into close proximity of the M15 mutant. Because each part of the enzyme was inactive by itself, only the secondary antibody-antigen-primary antibody complexes produced enzyme (β-gal) activity and thus eliminated many of the washing steps involved in standard ELISA assays.

A sandwich ELISA was used as an example but the ELISA can be of any format, or in general where proximity of the α-peptide and M15 mutant are used as a readout.

This system could work by proximity but also by immobilization. The complementation of the M15 mutant with the alpha peptide is normally a slow process thus the system may act to immobilize the alpha peptide in a position where it increases its ability to complement. In this case the complementation is a "presentation" issue. Thus by restraining the alpha peptide to certain configurations in physical space or orientation that increase its likelihood of binding the M15 mutant increases in enzyme activity can be obtained.

Example 6

ELISA Assay for Detecting Environmental Pollutants

Enzyme-linked immunoassay (ELISA) systems are available for detecting and measuring common environmental pollutants. This is of particular interest in the light of recent findings of high and potentially harmful levels of organochlorine compounds, such as PCBs, in some farmed salmon. Assays comprising four different enzyme-linked immunoassay (ELISA) systems for assaying vitellogenin in carp, fathead minnow, medaka, and zebrafish, as well as two enzyme immunoassays (EIAs) for PCB and coplanar-PCB, are available from Amersham Biosciences (Piscataway, N.J.). An enzyme-linked immunosorbent assay (ELISA) has been developed for the detection of the insecticide flucythrinate in environmental and food samples. See, e.g., Nakata et al., *Pest Manag. Sci.* 57:269-77 (2001). Analysis of Soil and Dust Samples for Polychlorinated Biphenyls by Enzyme-linked Immunosorbent Assay also has been reported. See, e.g., Chuang el al., *Analytica Chimica Acta,* 376:67-75 (1998).

A purified low-affinity fragment (e.g., M15 β-galactosidase) is coated onto a substrate such as a microwell plate along with fish cell samples suspected of containing a pollutant in each well. A primary (or monoclonal) antibody specific for the particular pollutant (antigen) is conjugated with the complementary low affinity fragment (alpha peptide) is added to each well. Presence of the pollutant in the fish cell sample is detected by β-galactosidase activity generated by the close proximity of the complementary low affinity fragments. As each complementary low-affinity fragment of the enzyme is inactive by itself only the formation of the antibody-antigen (pollutant) complexes produces enzyme (β-gal) activity and thus eliminating many of the washing steps involved in standard ELISA assays.

All publications and patent applications cited in this specification are herein incorporated by reference as if each individual publication or patent application were specifically and individually indicated to be incorporated by reference.

The invention claimed is:

1. A method to assess intracellular translocation of a protein of interest in a mammalian cell from a first subcellular compartment to a second subcellular compartment, comprising:
   (a) expressing a fusion protein in said first subcellular compartment, said fusion protein comprising said protein of interest and a β-galactosidase alpha fragment which either is (i) a truncation as shown in SEQ ID NO: 6 or (ii) is less than 56 amino acids in length and comprises an amino acid sequence as shown in SEQ ID NO: 1, provided that it has a point mutation in a region spanning residues H31 and E41;
   (b) expressing in said cell a β-galactosidase omega fragment localized to either (i) said first subcellular compartment or (ii) said second subcellular compartment, whereby
   (c) translocation of said fusion protein from said first subcellular compartment to said second subcellular compartment
      (i) decreases local concentration of said fusion protein and said omega fragment when the omega fragment is localized to the first subcellular compartment or
      (ii) increases local concentration of said fusion protein and said omega fragment when the omega fragment is localized to the second subcellular compartment, whereby
   (d) formation of active β-galactosidase occurs when said fusion protein and said omega fragment are in the same subcellular compartment, and
   (e) increasing or decreasing local concentration in step (c) results in a detectible signal from active β-galactosidase proportional to an amount of translocation.

2. The method of claim 1 wherein the β-galactosidase omega fragment and β-galactosidase alpha fragment are low affinity fragments of β-galactosidase and the intracellular translocation is between cytosol and a cell membrane.

3. The method of claim 1 wherein the β-galactosidase omega fragment and β-galactosidase alpha fragment are high affinity fragments and the intracellular translocation is between compartments separated by a membrane.

4. The method of claim 1 wherein said alpha fragment is selected from the group consisting of H31R (SEQ ID NO: 2), F34Y (SEQ ID NO: 3), E41Q (SEQ ID NO: 4), and N39D (SEQ ID NO: 5).

5. The method of claim 1 wherein said omega fragment is localized to a membrane by fusion with a peptide that localizes in a membrane.

6. The method of claim 5 wherein said fusion comprises a transmembrane region of an EGFR receptor.

7. The method of claim 5 wherein said omega fragment is localized to the nucleus.

8. The method of claim 7 wherein said fusion comprises a triplet SV40 nuclear localization signal.

9. The method of claim 1, wherein said alpha fragment is provided to the cell in an expression vector.

10. The method of claim 9, wherein said expression vector is a retroviral vector.

11. The method of claim 1, wherein said omega fragment is provided to the cell in an expression vector.

12. The method of claim 11, wherein said expression vector is a retroviral vector.

13. The method of claim 1, wherein said detectible signal is detected by flow cytometry.

14. The method of claim 1, wherein said detectible signal is detected by assessing luminescence.

15. The method of claim 1, wherein the intracellular translocation is inducible.

16. The method of claim 1, wherein the intracellular translocation is induced by an intracellular signal cascade.

17. The method of claim 1, wherein the intracellular translocation is induced in response to a hormone, cytokine, pharmaceutical agent, or external stressor.

18. A method according to claim 1 wherein the intracellular translocation is detected in real time using confocal microscopy.

19. The method of claim 1 further comprising the steps of contacting said mammalian cell with a modulator suspected of being able to influence the translocation of said protein and measuring a difference in signal produced in the presence of said modulator relative to signal produced in the absence of said modulator.

* * * * *